(12) United States Patent
Alfano et al.

(10) Patent No.: US 9,169,489 B2
(45) Date of Patent: Oct. 27, 2015

(54) TRANSGENIC SOYBEAN PLANTS EXPRESSING A SOYBEAN HOMOLOG OF GLYCINE-RICH PROTEIN 7 (GRP7) AND EXHIBITING IMPROVED INNATE IMMUNITY

(75) Inventors: James R. Alfano, Lincoln, NE (US); Anna Joe, Lincoln, NE (US); Thomas E. Clemente, Lincoln, NE (US); Zhengqing Fu, Cary, NC (US); Ming Guo, Lincoln, NE (US); Byeong-Ryool Jeong, Omaha, NE (US); Thomas Elthon, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 93 days.

(21) Appl. No.: 13/608,702

(22) Filed: Sep. 10, 2012

(65) Prior Publication Data
US 2013/0074217 A1    Mar. 21, 2013

Related U.S. Application Data

(60) Provisional application No. 61/532,526, filed on Sep. 8, 2011.

(51) Int. Cl.
*C12N 15/82* (2006.01)
*C07K 14/415* (2006.01)

(52) U.S. Cl.
CPC .......... *C12N 15/8279* (2013.01); *C07K 14/415* (2013.01); *C12N 15/8281* (2013.01)

(58) Field of Classification Search
None
See application file for complete search history.

(56) References Cited

U.S. PATENT DOCUMENTS

| | | | |
|---|---|---|---|
| 4,693,976 A | 9/1987 | Schilperoort et al. | |
| 4,762,785 A | 8/1988 | Comai | |
| 4,940,838 A | 7/1990 | Schilperoort et al. | |
| 4,945,050 A | 7/1990 | Sanford et al. | |
| 5,004,863 A | 4/1991 | Umbeck | |
| 5,104,310 A | 4/1992 | Saltin | |
| 5,141,131 A | 8/1992 | Miller, Jr. et al. | |
| 5,149,645 A | 9/1992 | Hoekema et al. | |
| 5,159,135 A | 10/1992 | Umbeck | |
| 5,177,010 A | 1/1993 | Goldman et al. | |
| 5,231,019 A | 7/1993 | Paszkowski et al. | |
| 5,302,523 A | 4/1994 | Coffee et al. | |
| 5,384,253 A | 1/1995 | Krzyzek et al. | |
| 5,463,174 A | 10/1995 | Moloney et al. | |
| 5,464,763 A | 11/1995 | Schilperoort et al. | |
| 5,464,765 A | 11/1995 | Coffee et al. | |
| 5,469,976 A | 11/1995 | Burchell | |
| 5,472,869 A | 12/1995 | Krzyzek et al. | |
| 5,641,664 A | 6/1997 | D'Halluin et al. | |
| 5,679,558 A | 10/1997 | Göbel et al. | |
| 5,712,135 A | 1/1998 | D'Halluin et al. | |
| 6,002,070 A | 12/1999 | D'Halluin et al. | |
| 6,074,877 A | 6/2000 | D'Halluin et al. | |
| 2006/0048240 A1* | 3/2006 | Alexandrov et al. | 800/278 |
| 2008/0028487 A1 | 1/2008 | Alfano et al. | |

FOREIGN PATENT DOCUMENTS

WO    WO 87/06614    11/1987

OTHER PUBLICATIONS

Fu et al. A type III effector ADP-ribosylates RNA-binding proteins and quells plant immunity. 2007. Nature. 44:284-289.*
Xu et al. Separation and identification of soybean leaf proteins by two-dimensional gel electrophoresis and mass spectrometry. 2006. Phytochemistry. 67:2431-2440.*
Jeong et al. Structure function analysis of an ADP-ribosyltransferase type III effector and its RNA-binding target in plant immunity. 2011. J. Biol. Chem. 286:43272-43281.*
Guo et al. Protein tolerance to random amino acid change. 2004. PNAS. 101(25):9205-9210.*
Alfano, "Roadmap for future research on plant pathogen effectors," Mol. Plant Pathol., 2009, 10(6):805-13.
Benfey & Chua, "The Cauliflower Mosaic Virus 35S Promoter: Combinatorial Regulation of Transcription in Plants," *Science*, 1990, 250:959-66.
Block & Alfano, "Plant targets for *Pseudomonas syringae*type III effectors: virulence targets or guarded decoys?" *Curr. Opin. Microbiol.*, 2011, 14(1):39-46.
Block et al., "Phytopathogen type III effector weaponry and their plant targets," *Curr. Opin. Plant. Biol.*, 2008, 11(4):396-403
Block et al., "The *Pseudomonas syringae*type III effector HopG1 targets mitochondria, alters plant development and suppresses plant innate immunity," *Cell Microbiol.*, 2010, 12(3):318-30.
Chinchilla et al., "The *Arabidopsis*Receptor Kinase FLS2 Binds flg22 and Determines the Specificity of Flagellin Perception," *Plant Cell*, 2006, 18:465-76.
Crabill et al., "Plant immunity directly or indirectly restricts the injection of type III effectors by the *Pseudomonas syringae*type III secretion system," *Plant Physiol.*, 2010, 154(1):233-44.
Freeman et al., "Quantitative RT-PCR: Pitfalls and Potential," *Biotechniques*, 1999, 26:112-122 & 124-125.
Fu et al., "A type III effector ADP-ribosylates RNA-binding proteins and quells plant immunity," *Nature*, 2007, 447:284-288. Fu et al., "*Pseudomonas syringae*HrpJ is a type III secreted protein that is required for plant pathogenesis, injection of effectors, and secretion of the HrpZ1 Hairpin," *J. Bacteriol.*, 2006, 188(17):6060-9.
Guo et al., "The majority of the type III effector inventory of *Pseudomonas syringae*pv. tomato DC3000 can suppress plant immunity," *Mol. Plant Microbe Interact.*, 2009, 22(9):1069-80.
Hajdukiewicz et al., "The small, versatile*pPZP* family of *Agrobacterium*binary vectors for plant transformation," *Plant Mol. Biol.*, 1994, 25:989-94.
Hann et al., "Early events in the pathogenicity of *Pseudomonas syringae*on *Nicotiana benthamiana*," *Plant J.*, 2007, 49:607-618.
Hinchee et al., "Production of Transgenic Soybean Plants Using *Agrobacterium*-Mediated DNA Transfer," *Bio/Technol.*, 1988, 6:915-22.
Jeong et al., "Structure Function Analysis of an ADP-ribosyltransferase Type III Effector and it RNA-binding Target in Plant Immunity," *J. Biol. Chem.*, 2011, 286:43272-81.
Kim et al., "Glycine-rich RNA-binding protein7 affects abiotic stress responses by regulating stomata opening and closing in *Arabidopsis thaliana*," *Plant J.*, 2008, 55:455-466.
Lefebvre et al., "A remorin protein interacts with symbiotic receptors and regulates bacterial infection," *Proc Natl Acad Sci USA*, 2010, 107:2343-2348.

(Continued)

*Primary Examiner* — Vinod Kumar
(74) *Attorney, Agent, or Firm* — Fish & Richardson P.C.

(57) ABSTRACT

This disclosure provides for transgenic soybean plants expressing a soybean homolog of glycine-rich protein 7 (GRP7) and exhibiting improved innate immunity and methods of making such plants.

7 Claims, 20 Drawing Sheets

(56) References Cited

OTHER PUBLICATIONS

Schwessinger et al., "Phosphorylation-Dependent Differential Regulation of Plant Growth, Cell Death, and Innate Immunity by the Regulatory Receptor-Like Kinase BAK1," PLoS Genet., 2011, 7:e1002046.

Streitner et al., "The small glycine-rich RNA binding protein ATGRP7 promotes floral transition in Arabidopsis thaliana," Plant J., 2008, 56:239-50.

Thompson et al., "Characterization of the herbicide-resistance gene bar from Streptomyces hygroscopicus," EMBO, 1987, 6:2519-23.

van der Biezen et al., "ArabidopsisRelA/SpoT homologs implicate (p)ppGpp in plant signaling," PNAS USA, 2000, 97:3747-52.

Vencato et al., "Bioinformatic-enabled identification of the HrpL regulon and type III secretion system effector proteins of Pseudomonas syringae pv. Phaseolicola 1448A," Mol. Plant Microbe Interact., 2006, 19(11):1193-206.

Walton et al., "Effectors, effectors et encore des effectors: the XIV International Congress of Molecular-Plant Microbe Interactions, Quebec," Mol. Plant Microbe Interact., 200922(12):1479-83.

Wei et al., "A Pseudomonas syringaepv. Tomato DC3000 mutant lacking the type III effector HopQ1-1 is able to cause disease in the model plant Nicotiana benthamiana," Plant J., 51(1):32-46.

Zipfel et al., "Bacterial disease resistance in Arabidopsis through flagellin perception," Nature, 2004, 428:764-767.

Zipfel et al., "Perception of the Bacterial PAMP EF-Tu by the Receptor EFR Restricts Agrobacterium-Mediated Transformation," Cell, 2006, 125:749-760.

Zuo et al., "An estrogen receptor-based transactivator XVE mediates highly inducible gene expression in transgenic plants," Plant J., 2000, 24:265-273.

Hou et al., "The multilevel and dynamic interplay between plant and pathogen," Plant Signaling & Behavior, Apr. 2009, 4(4):283-293.

Streitner et al., "Global transcript profiling of transgenic plants constitutively overexpressing the RNA-binding protein AtGRP7," BMC Plant Biology, 2010, 10:221.

* cited by examiner

SEQ ID NO: 15 & 16
Glyma05g00400.1

ATGGCTTTCTTTGGTAGAATTGGGAATTTATTAAGACAGACAGCAAGCAGGCAGGTTAGTTCAGAATTGC
GATCATCCCCTTCGTTTTTTCAGGCTATACGCAGTATGTCATCTGCTCCAAGCACAAAGCTGTTTATCGG
AGGTGTTTCATATTCTACTGACGAGCAAAGTTTGAGGGAAGCTTTTTCAAAATATGGTGAAGTTGTTGAT
GCTAGGATAATTATGGATCGTGAAACTGGTAGATCCAGAGGATTTGGCTTTATTACATACACTTCGGTTG
AGGAGGCATCAAGTGCCATTCAGGCCTTGGATGGTCAGGACCTACATGGTCGCCCGATTAGGGTGAATTA
TGCTAATGAAAGACCTCGTGGATATGGTGGCGGTGGCTTTGGTTCATACGGTGCTGTAGGTGGCGGTGGC
TATGAAGGTGGTAGCAGCTATCGTGGTGGTTATGGTGGTGACAACTATAGTCGAAATGATGGGAGTGGTT
ATGGATATGGTGGAGGCAGGTATGGATCAGGCGGCAATTATGGGGACAGTGGCTCTGGCAATAACTATTC
AGGAGGCTATGCTGGTAATGCCGGTGGTGTAGGCAATCATGAAAGCTCTACTGGTTTTGCCAGTAATGGA
TATGATGGAAGTGTTGTGGATGGTGGTGTTGGTGCAGGTAGTGGCACTAGCTTTGCTGATGGCTATGATG
GAAGTGCGGGGTCTGAATTTGGCAGCAGTGGCCAATTAGATAGCAAAGCAAGCAGCAAAGGAGATGAGGA
TTTTGGTGATTACAGGGATGACAACGATGCAGATGATTTTGCCAAGAGGGCTTGA

MAFFGRIGNLLRQTASRQVSSELRSSPSFFQAIRSMSSAPSTKLFIGGVSYSTDEQSLREAFSKYGEVVD
ARIIMDRETGRSRGFGFITYTSVEEASSAIQALDGQDLHGRPIRVNYANERPRGYGGGGFGSYGAVGGGG
YEGGSSYRGGYGGDNYSRNDGSGYGYGGGRYGSGGNYGDSGSGNNYSGGYAGNAGGVGNHESSTGFASNG
YDGSVVDGGVGAGSGTSFADGYDGSAGSEFGSSGQLDSKASSKGDEDFGDYRDDNDADDFAKRA*

SEQ ID NO: 17 & 18
Glyma05g00400.2

ATGGCTTTCTTTGGTAGAATTGGGAATTTATTAAGACAGACAGCAAGCAGGCAGGTTAGTTCAGAATTGC
GATCATCCCCTTCGTTTTTTCAGGCTATACGCAGTATGTCATCTGCTCCAAGCACAAAGCTGTTTATCGG
AGGTGTTTCATATTCTACTGACGAGCAAAGTTTGAGGGAAGCTTTTTCAAAATATGGTGAAGTTGTTGAT
GCTAGGATAATTATGGATCGTGAAACTGGTAGATCCAGAGGATTTGGCTTTATTACATACACTTCGGTTG
AGGAGGCATCAAGTGCCATTCAGGCCTTGGATGGTCAGGACCTACATGGTCGCCCGATTAGGGTGAATTA
TGCTAATGAAAGACCTCGTGGATATGGTGGCGGTGGCTTTGGTTCATACGGTGCTGTAGGTGGCGGTGGC
TATGAAGGTGGTAGCAGCTATCGTGGTGGTTATGGTGGTGACAACTATAGTCGAAATGATGGGAGTGGTT
ATGGATATGGTGGAGGCAATCATGAAAGCTCTACTGGTTTTGCCAGTAATGGATATGATGGAAGTGTTGT
GGATGGTGGTGTTGGTGCAGGTAGTGGCACTAGCTTTGCTGATGGCTATGATGGAAGTGCGGGGTCTGAA
TTTGGCAGCAGTGGCCAATTAGATAGCAAAGCAAGCAGCAAAGGAGATGAGGATTTTGGTGATTACAGGG
ATGACAACGATGCAGATGATTTTGCCAAGAGGGCTTGA

MAFFGRIGNLLRQTASRQVSSELRSSPSFFQAIRSMSSAPSTKLFIGGVSYSTDEQSLREAFSKYGEVVD
ARIIMDRETGRSRGFGFITYTSVEEASSAIQALDGQDLHGRPIRVNYANERPRGYGGGGFGSYGAVGGGG
YEGGSSYRGGYGGDNYSRNDGSGYGYGGGNHESSTGFASNGYDGSVVDGGVGAGSGTSFADGYDGSAGSE
FGSSGQLDSKASSKGDEDFGDYRDDNDADDFAKRA*

SEQ ID NO: 19 & 20
Glyma08g26900.1

ATGGCGTTCTTAAATAAAATTGGAAATCTGGTCAAGAATTCTGCTGTCAAGCACATCAATCAAGATTTTT
CAGTGTCTACCCCATCACTTTTCCAAGCAATTAGATCCATGTCATCTGCAAAGCTTTTTGTCGGAGGTAT
TTCTTACAGCACTGATGATATGAGTTTGCGAGAGTCTTTTGCTCGCTATGGAGAAGTAATAGATGTCAAG

Figure 16-1

```
GTCATTATGGATCGTGAAACTGGCAGGTCAAGAGGTTTTGGCTTCATAACTTTTGCAACAAGTGAGGATG
CATCTTCTGCCATTCAGGGCATGGATGGTCAGGATCTTCATGGTCGCAGGATACGGGTGAATTATGCTAC
AGAAAGGTCACGTCCAGGGTTTGGTGGTGATGGTGGATATAGGGGCAGTGGTGGCAGCGATGGCTACAAT
AGGGGTGGAAACTATGGAGGTGGATATAACAGTGGCAGCGATGGCTACAATAGGGGTGGAAACTATGGAA
GTGGCAATTATAATGTTACAAGCAGCTATAGTGATGGCAATGCTGAAACTAGTTACACTAGTGGTGCTAA
TGCTGGTAATTACCAATTCAATGAAAATTCTGGTGGAGTTTTTGGCTCAGCTAGCGGTGAATTCAGCAGC
AACCAAAATGACGCAACAGGTGCAGACAATGATGAATTCATTGAGCCACTTGAAGACAATGTGAGGGAGA
ACAATGATGAACCTACTGACTACGCTCAGAACCGCTGA

MAFLNKIGNLVKNSAVKHINQDFSVSTPSLFQAIRSMSSAKLFVGGISYSTDDMSLRESFARYGEVIDVK
VIMDRETGRSRGFGFITFATSEDASSAIQGMDGQDLHGRRIRVNYATERSRPGFGGDGGYRGSGGSDGYN
RGGNYGGGYNSGSDGYNRGGNYGSGNYNVTSSYSDGNAETSYTSGANAGNYQFNENSGGVFGSASGEFSS
NQNDATGADNDEFIEPLEDNVRENNDEPTDYAQNR*
```

SEQ ID NO: 21 & 22
Glyma11g36580.1

```
ATGGCCTTCTGTAATAAGGTTGGAAATGTCTTGAGGCAGGGTGCTGCTCGCAGCACACAAGCACCTGTTT
CATCCATGCTTAATTACATTCGCTGCATGTCTTCAAGCAAGCTTTTTATTGGAGGCCTTTCATATGGAGT
TGACGATCAGTCTCTTAAGGATGCATTTTCTGGCTTTGGAGATGTGGTTGATGCAAAAGTTATAACTGAC
AGAGACTCTGGAAGATCAAGGGGATTTGGATTTGTCAACTTCTCCAATGATGAGTCTGCAAGTTCGGCAC
TCTCTGCAATGGATGGGAAGATGGGCGAAGCATTAGGGTATCCTATGCAAATGATAGACCTTCTGGACCT
CAATCTGGCGGCGGCGGCGGTGGTGGTTATCGCAGTGGGGGTTTTGGCGGCGGGTGGTGATTTTGCTTCT
CGCAATGGTGGTTGGTGA

MAFCNKVGNVLRQGAARSTQAPVSSMLNYIRCMSSSKLFIGGLSYGVDDQSLKDAFSGFGDVVDAKVITD
RDSGRSRGFGFVNFSNDESASSALSAMDGKMGEALGYPMQMIDLLDLNLAAAAVVVIAVGVLAAGGDFAS
RNGGW*
```

SEQ ID NO: 23 & 24
Glyma17g08630.1

```
ATGGCTTTCTTTGGTAGAATTGGGAATTTGTTACGACAGACAGCGAGCAGGCAGGTTAGTTCAAAATTGC
GTTCGCCCCCTTCATTTTTTCAGGCTATACGCTGTATGTCATCTGCCCCAAGCACAAAACTGTTTATTGG
AGGTGTTTCATATTCTACTGACGAGCAAAGCTTGAGGGAAGCTTTTTCAAAATATGGTGAAGTTGTTGAT
GCTCGGATAATTATGGATCGTGAAACTGGTAGATCCAGAGGATTTGGCTTTATTACATACACTTCGGTTG
AGGAGGCATCAAGTGCCATTCAGGCCTTGGATGGTCAGGATCTTCATGGTCGCCCAATTAGGGTGAATTA
TGCTAATGAAAGACCTCGTGGATATGGTGGTGGTGGCGGCGGCTTTGGTTCATATGGTGCTGTAGGTGGC
GGTGGTTATGAAGGTGGTGGTGGCAGCGGTTATCGTGGAAATGTTTCTGATGGTTATGGTGGTGGCAACT
ATAGTCGAAATGATGGGGGTGGTTATGGATATGGTGCAGGCAGTTATGGATCAGGCGGCAATTATGGGGA
CAGTGGCCCTGGCAATAACTACTCGGGAGGCTATAGTGGTAGTAACAGTGGACATTTTGGTGATGCCGGT
AGTGTAGGCAATCATGAAAGCTCTACTGGTTTTGCCGGTAATGGATATGATGGAAGTGTCGTGGATGGCG
GTGTTGGTGCAGGGTCGGAATTTGGCAGCAGTGGCCAATTAGATAGCAAAACAAGCAGCAATGGAGATGA
GGGTTTTGGGGATTACAGGGATGACAACGATGCAGATAATTTTGCCAAGAGGGCTTGA

MAFFGRIGNLLRQTASRQVSSKLRSPPSFFQAIRCMSSAPSTKLFIGGVSYSTDEQSLREAFSKYGEVVD
ARIIMDRETGRSRGFGFITYTSVEEASSAIQALDGQDLHGRPIRVNYANERPRGYGGGGGFGSYGAVGG
```

Figure 16-2

GGYEGGGGSGYRGNVSDGYGGGNYSRNDGGGYGYGAGSYGSGGNYGDSGPGNNYSGGYSGSNSGHFGDAG
SVGNHESSTGFAGNGYDGSVVDGGVGAGSEFGSSGQLDSKTSSNGDEGFGDYRDDNDADNFAKRA*

SEQ ID NO: 25 & 26
Glyma18g00480.1

ATGGCGTTCTGTAATAAGGTTGGAAATGTCTTGAGGCAGGGTGCTGCTCGCAGCACACATGCCCCTGTTG
CGTCCATGCTTAATTACATCCGCTGCATGTCTTCAAGCAAGCTTTTCATTGGAGGCCTTTCATATGGAGT
TGATGACCAGTCTCTTAAGGATGCATTTTCTGGCTTTGGAGATGTGGTTGATGCAAAAGTTATAACTGAT
AGAGACAGTGGAAGATCAAGGGGATTTGGATTTGTCAACTTCTCCAATGATGAGTCTGCAAGTTCGGCAC
TCTCTGCAATGGACGGGAAGGATCTAAATGGGCGAAGCATTCGGGTATCCTATGCAAATGATAAACCATC
TGCACCTCGACCTGGTGGCGGTGGCGGTTATCGTGGCGGGGATTATGATGGTGATTTTGCTTCTCGTAGT
GGTGGTTGGTGA

MAFCNKVGNVLRQGAARSTHAPVASMLNYIRCMSSSKLFIGGLSYGVDDQSLKDAFSGFGDVVDAKVITD
RDSGRSRGFGFVNFSNDESASSALSAMDGKDLNGRSIRVSYANDKPSAPRPGGGGGYRGGDYDGDFASRS
GGW*

SEQ ID NO: 27 & 28
Glyma18g00480.2

ATGGCGTTCTGTAATAAGGTTGGAAATGTCTTGAGGCAGGGTGCTGCTCGCAGCACACATGCCCCTGTTG
CGTCCATGCTTAATTACATCCGCTGCATGTCTTCAAGCAAGCTTTTCATTGGAGGCCTTTCATATGGAGT
TGATGACCAGTCTCTTAAGGATGCATTTTCTGGCTTTGGAGATGTGGTTGATGTTATAACTGATAGAGAC
AGTGGAAGATCAAGGGGATTTGGATTTGTCAACTTCTCCAATGATGAGTCTGCAAGTTCGGCACTCTCTG
CAATGGACGGGAAGGATCTAAATGGGCGAAGCATTCGGGTATCCTATGCAAATGATAAACCATCTGCACC
TCGACCTGGTGGCGGTGGCGGTTATCGTGGCGGGGATTATGATGGTGATTTTGCTTCTCGTAGTGGTGGT
TGGTGA

MAFCNKVGNVLRQGAARSTHAPVASMLNYIRCMSSSKLFIGGLSYGVDDQSLKDAFSGFGDVVDVITDRD
SGRSRGFGFVNFSNDESASSALSAMDGKDLNGRSIRVSYANDKPSAPRPGGGGYRGGDYDGDFASRSGG
W*

SEQ ID NO: 29 & 30
Glyma18g50150.1

ATGGCGTTCTTAAATAAAATTGGAAATCTGCTCAAGAATTCTGCTGTCAAGCACATCAATCAGGATTTTT
CGGCGTCTACCCCTTCACTTTTCCAAGCAATTAGATCCATGTCATCTGCAAAGCTTTTCGTCGGAGGTAT
TTCTTACAGCACTGATGATATGAGTTTGCGAGAGTCTTTTGCTCGCTATGGAGAAGTAATTGATGGCAAG
GTTATTATGGATCGTGAAACTGGCAGGTCAAGAGGTTTTGGCTTTGTAACTTTTGCAACAAGTGAGGATG
CATCTTCTGCCATTCAGGGCATGGATGGCCAGGATCTTCATGGTCGGAGGATACGGGTGAATTATGCTAC
AGAAAGGTCACGTCCAGGGTTTGGTGGTGATGGTGGATATGGCAGTGGTGGTGGTGGCTACAATGGGGGT
GGAAACTATGGAAGTGGAGGTGGATATGGTGGTGGTGGTGGCTATAATAGGGGTGGAAACTATGGAAGTG
GCGGTTATAATGTTACTAGCAGCTATAGTGGTGGCAATGCTGAAACTAGTTACACTGGTGGTGGTAATGC
TAGTAATTACCAATTCAATGAAAACTCTGGTGGAGATTTTGGCTCAGCTAGCGGTGAATTCAGCAGCAAC
CAAAATGACACAGCAGGTGCAGACAATGATGAATTCATTGAGCCACTTGAAGACAATGTGAGGGAGAACA
ATGATGGACCTACCGACTACGCTCAGAACCGCTGA

Figure 16-3

MAFLNKIGNLLKNSAVKHINQDFSASTPSLFQAIRSMSSAKLFVGGISYSTDDMSLRESFARYGEVIDGK
VIMDRETGRSRGFGFVTFATSEDASSAIQGMDGQDLHGRRIRVNYATERSRPGFGGDGGYGSGGGGYNGG
GNYGSGGGYGGGGGYNRGGNYGSGGYNVTSSYSGGNAETSYTGGGNASNYQFNENSGGDFGSASGEFSSN
QNDTAGADNDEFIEPLEDNVRENNDGPTDYAQNR*

SEQ ID NO: 31 & 32
Glyma06g01470.1

ATGGCTTCTGCAGAAGTAGAGTTCCGATGCTTTGTTGGTGGGCTTGCTTGGGCCACCGACCACGATGCTC
TCGAGAAAGCCTTCTCTCAATTTGGCGAAATCGTCGAATCGAAGGTCATCAACGATCGTGAAACTGGAAG
ATCCAGAGGGTTTGGATTTGTGACCTTCGCCACAGAGCAGGCGATGAGAGACGCAATTGAAGGAATGAAC
GGCCAGAACCTCGACGGTCGTAATATAACCGTGAACGAGGCTCAATCCCGTGGAAAAGGTGGCGGCGGCG
GCGGCGGCGGCTACGGAGGAGGTGGTGGTGGTTACGGTGGCGGCGGAGGTTACAGCCGCGGTGGAGGAGG
ATATGGTGGCGGAGGAGGCCGCCGTGAAGGTGGTTATAACCGCAACGGTGGTGGAGGAGGATATGGTGGC
GGTGGCGGCGGATATGGAGGTGGTGGAGGTTATGGTGGCGGTGGGAGAGACCGTGGATATGGTGGTGATG
GTGGGTCCCGCTACTCGAGAGGAGGCGGTGGTTCGGATGGAGGAAGCTGGAGGAATTAA

MASAEVEFRCFVGGLAWATDHDALEKAFSQFGEIVESKVINDRETGRSRGFGFVTFATEQAMRDAIEGMN
GQNLDGRNITVNEAQSRGKGGGGGGGYGGGGGYGGGGYSRGGGYGGGGRREGGYNRNGGGGYGG
GGGGYGGGGYGGGGRDRGYGGDGGSRYSRGGGGSDGGSWRN*

SEQ ID NO: 33 & 34
Glyma11g12480.1

ATGGCTTCTGCGGATGTTGAATACCGATGCTTTGTTGGTGGGCTCGCTTGGGCCACTGACAACTACGATC
TGGAGAAAGCCTTCTCTCAGTACGGTGACGTCGTTGAATCGAAGATTATCAACGATCGTGAGACTGGAAG
ATCCAGGGGATTTGGATTTGTTACCTTCGCCTCCGAGGATTCAATGAGGGATGCGATCGAAGGGATGAAC
GGTCAGAACCTTGATGGACGCAACATCACTGTGAACGAAGCTCAGTCCCGCGGAAGCCGCGGTGGAGGCG
GTGGCGGTTACGGAAGTGGCGGTGGATACAACCGCAGTGGTGGTGCTGGAGGATACGGTGGCCGTCGGGA
AGGTGCATATAACCGTAACGGTGGTGGTTATGGCGGTGACAGAGACCATCGTTACGGACCTTACGGGGAC
GGTGGATCACGCTACTCGTGGTGGTGGTGATGGAAGCTGGAGAAATTAG

MASADVEYRCFVGGLAWATDNYDLEKAFSQYGDVVESKIINDRETGRSRGFGFVTFASEDSMRDAIEGMN
GQNLDGRNITVNEAQSRGSRGGGGGYGSGGGYNRSGGAGGYGGRREGAYNRNGGGYGGDRDHRYGPYGD
GGSRYSRGGGDGSWRN*

SEQ ID NO: 35 & 36
Glyma11g12490.1

ATGTTATCCATGGCTTCTGCATATGTTGAGTACCGTTGCTTTGTTGGTGGGCTCGCTTGGGCCACAGACG
ATCATGCCTTGGAGAAAGCCTTCTCTCACTACGGCAACATCGTTAATCGAAGATTATCAACGATCGTGA
GACCGGAAGGTCCAGGGGATTTGGATTTGTTACCTTCGCCTCGGAGAATTCAATGAAGGATGCGATCGAA
GGGATGAACGGTCAGAACCTTGACGGACGTAACATAACTGTGAACGAAGCTCAGTCCCGCGGCAGCCGCG
GTGGATACGGTGGTCGTCGTGAAGGTGGATATAACCGTGGTGGTGGAGGCTATGGAGGGGTGGTTATGG
TGGTGACAGAGATTGTGGTTACGGTGACGGTGGTTCACGCTACTCGTGGTGGCGATGTCAATGGAAGC
CGGAGAAACTAG

Figure 16-4

MLSMASAYVEYRCFVGGLAWATDDHALEKAFSHYGNIVESKIINDRETGRSRGFGFVTFASENSMKDAIE
GMNGQNLDGRNITVNEAQSRGSRGGYGGRREGGYNRGGGGYGGGGYGGDRDCGYGDGGSRYSRGGDVNGS
RRN*

SEQ ID NO: 37 & 38
Glyma11g12510.2

ATGGCTTCTGCAGATGTTGAGTTCCGTTGCTTTGTTGGTGGGCTTGCTTGGGTCACCGGCAACGATGCCC
TCGAGAAAGCCTTTTCAATCTACGGCGACATCGTTGAATCGAAGGTTATCAACGACCGTGAGACTGGAAG
GTCCAGAGGATTCGGATTTGTGACCTTCGCCTCAGAGCAGTCAATGAAAGATGCGATCGCAGGAATGAAC
GGCCAGGACCTTGACGGCCGTAACATCACTGTCAACGAAGCTCAGACCCGCGCCAGCCGTGGTGGTGGTG
GAGGCGGTGGTTTCGGAAGTGGTGGAGGATACGGCGGTGGTAGAGACCGTGGTTACGGTGGTGATGGTGG
TTCTCGCTACTCTCGCGGTGGGGAAGGCGGTGGATCCGATGGAAACTGGAGAAATTAG

MASADVEFRCFVGGLAWVTGNDALEKAFSIYGDIVESKVINDRETGRSRGFGFVTFASEQSMKDAIAGMN
GQDLDGRNITVNEAQTRASRGGGGGGFGSGGGYGGGRDRGYGGDGGSRYSRGGEGGGSDGNWRN*

SEQ ID NO: 39 & 40
Arabidopsis thaliana GRP7

CTTCGTCTACATCGTTCTACACATCTCACTGCTCACTACTCTCACTGTAATCCCTTAGATCTTCTTTTCA
AATTTCAATGGCGTCCGGTGATGTTGAGTATCGGTGCTTCGTTGGAGGTCTAGCATGGGCCACTGATGAC
AGAGCTCTTGAGACTGCCTTCGCTCAATACGGCGACGTTATTGATTCCAAGATCATTAACGATCGTGAGA
CTGGAAGATCAAGGGGATTCGGATTCGTCACCTTCAAGGATGAGAAAGCCATGAAGGATGCGATTGAGGG
AATGAACGGACAAGATCTCGATGGCCGTAGCATCACTGTTAACGAGGCTCAGTCACGAGGAAGCGGTGGC
GGCGGAGGCCACCGTGGAGGTGGTGGCGGTGGATACCGCAGCGGCGGTGGTGGAGGTTACTCCGGTGGAG
GTGGTAGCTACGGAGGTGGCGGCGGTAGACGCGAGGGTGGAGGAGGATACAGCGGCGGCGGCGGCGGTTA
CTCCTCAAGAGGTGGTGGTGGCGGAAGCTACGGTGGTGGAAGACGTGAGGGAGGAGGAGGATACGGTGGT
GGTGAAGGAGGAGGTTACGGAGGAAGCGGTGGTGGTGGAGGATGGTAATTCCTTTAATTAGGTTTGGGAT
TACCAATGAATGTTCTCTCTCTCGCTTGTTATGCTTCTACTTGGTTTTGTGTGTTCTCTATTTTGTTCTG
GTTCTGCTTTAGATTTGATGTAACAGTTCGTGATTAGGTATTTTGGTATCTGGAAACGTAATGTTAAGTC
ACTTGTCATTCTCTAAATAACAAATTTCTTCGGAGATATTATCTCTGTTGATTGATTCTATCATCT

MASGDVEYRCFVGGLAWATDDRALETAFAQYGDVIDSKIINDRETGRSRGFGFVTFKDEKAMKDAIEGMN
GQDLDGRSITVNEAQSRGSGGGGHRGGGGGGYRSGGGGGYSGGGGSYGGGGRREGGGGYSGGGGGYSS
RGGGGGSYGGGRREGGGGYGGGEGGGYGGSGGGGGW

Figure 16-5

TRANSGENIC SOYBEAN PLANTS EXPRESSING A SOYBEAN HOMOLOG OF GLYCINE-RICH PROTEIN 7 (GRP7) AND EXHIBITING IMPROVED INNATE IMMUNITY

CROSS REFERENCE TO RELATED APPLICATIONS

This application claims benefit under 35 U.S.C. 119(e) to U.S. Application No. 61/532,526 filed Sep. 8, 2011, the entirety of which is incorporated by reference herein.

FEDERALLY SPONSORED RESEARCH OR DEVELOPMENT

The U.S. Government has certain rights in this invention pursuant to Grant No. R01 AI069146 awarded by the National Institute of Health.

TECHNICAL FIELD

This disclosure generally relates to soybean plants that have been genetically-engineered to improve their innate immunity.

BACKGROUND

The phytopathogenic bacterium, *Pseudomonas syringae*, can suppress both pathogen-associated molecular pattern (PAMP)-triggered immunity (PTI) and effector-triggered immunity (ETI) by the injection of type III effector (T3E) proteins into host cells. T3Es achieve immune suppression using a variety of strategies including interference with immune receptor signaling, blocking RNA pathways and vesicle trafficking, and altering organelle function.

Based, at least in part on the experimental results described herein, this disclosure provides compositions and methods that can be used to genetically engineer plants (e.g., soybean plants) that are able to exploit this interaction, thereby increasing the innate immunity of the plants.

SUMMARY

In one aspect, a method of increasing the innate immunity exhibited by a soybean plant is provided. Such a method typically includes introducing a transgene into a plurality of soybean cells to produce transgenic soybean cells, wherein the transgene comprises a nucleic acid sequence having at least 95% sequence identity to a sequence selected from the group consisting of SEQ ID NO: 15, 17, 19, 21, 23, 25, 27, 29, 31, 33 and 35, wherein the nucleic acid sequence is operably linked to a promoter functional in soybean cells; regenerating transgenic soybean plants from the transgenic soybean cells; and identifying at least one of the transgenic soybean plants expressing the transgene. Generally, the at least one of the transgenic soybean plants exhibits increased innate immunity in response to at least one biotic stress relative to a control plant.

In one embodiment, the transgene comprises a nucleic acid sequence having at least 99% sequence identity to a sequence selected from the group consisting of SEQ ID NO: 15, 17, 19, 21, 23, 25, 27, 29, 31, 33 and 35. In another embodiment, the transgene comprises a nucleic acid sequence having a sequence selected from the group consisting of SEQ ID NO: 15, 17, 19, 21, 23, 25, 27, 29, 31, 33 and 35. In some embodiments, the at least one biotic stress includes a pathogen such as, without limitation, bacteria, fungi, protozoa a virus, an insect, or a wound such as, without limitation, physical damage caused by people. In some embodiments, the promoter is a constitutive promoter.

In another aspect, a method of increasing the innate immunity exhibited by a soybean plant is provided. Such a method typically includes introducing a transgene into a plurality of soybean cells to produce transgenic soybean cells, wherein the transgene comprises a nucleic acid sequence that encodes a polypeptide having an amino acid sequence selected from the group consisting of SEQ ID NO: 16, 18, 20, 22, 24, 26, 28, 30, 32, 34 and 36, wherein the nucleic acid sequence is operably linked to a promoter functional in soybean cells; regenerating transgenic soybean plants from the transgenic soybean cells; and identifying at least one of the transgenic soybean plants expressing the transgene. Generally, the at least one of the transgenic soybean plants exhibits increased innate immunity in response to at least one biotic stress relative to a control plant.

In some embodiments, the at least one biotic stress includes a pathogen such as, without limitation, bacteria, fungi, protozoa a virus, and an insect, or a wound such as, without limitation, physical damage caused by people. In some embodiments, wherein the promoter is a constitutive promoter In still another aspect, a transgenic soybean plant comprising a transgene is provided. Typically, the transgene comprises a nucleic acid sequence having at least 95% sequence identity to a sequence selected from the group consisting of SEQ ID NO: 15, 17, 19, 21, 23, 25, 27, 29, 31, 33 and 35 operably linked to a promoter functional in soybean plants. Generally, the transgenic soybean plant exhibits an increase in innate immunity.

In some embodiments, the transgene comprise a nucleic acid sequence having at least 99% sequence identity to a sequence selected from the group consisting of SEQ ID NO: 15, 17, 19, 21, 23, 25, 27, 29, 31, 33 and 35. In some embodiments, the transgene comprises a nucleic acid sequence selected from the group consisting of SEQ ID NO: 15, 17, 19, 21, 23, 25, 27, 29, 31, 33 and 35. Also provided is seed from such a transgenic plant.

In yet another aspect, a transgenic soybean plant comprising a transgene is provided. Typically, the transgene comprises a nucleic acid sequence that encodes a polypeptide having an amino acid sequence selected from the group consisting of SEQ ID NO: 16, 18, 20, 22, 24, 26, 28, 30, 32, 34 and 36 operably linked to a promoter functional in soybean plants. Generally, the transgenic soybean plant exhibits an increase in innate immunity. Also provided is seed from such a transgenic plant.

In another aspect, an isolated nucleic acid having at least 95% sequence identity to a sequence selected from the group consisting of SEQ ID NO: 15, 17, 19, 21, 23, 25, 27, 29, 31, 33 and 35 is provided. In some embodiments, the isolated nucleic acid has at least 99% sequence identity to a sequence selected from the group consisting of SEQ ID NO: 15, 17, 19, 21, 23, 25, 27, 29, 31, 33 and 35. In some embodiments, the isolated nucleic acid has a sequence selected from the group consisting of SEQ ID NO: 15, 17, 19, 21, 23, 25, 27, 29, 31, 33 and 35. Also provided is a vector comprising such an isolated nucleic acid. In some embodiments, the isolated nucleic acid encodes a polypeptide having an amino acid sequence selected from the group consisting of SEQ ID NO: 16, 18, 20, 22, 24, 26, 28, 30, 32, 34 and 36, respectively.

In still another aspect, a purified polypeptide is provided. Such a polypeptide typically has at least 95% sequence identity to a sequence selected from the group consisting of SEQ ID NO: 16, 18, 20, 22, 24, 26, 28, 30, 32, 34 and 36. In some embodiments, the purified polypeptide has at least 99% sequence identity to a sequence selected from the group consisting of SEQ ID NO: 16, 18, 20, 22, 24, 26, 28, 30, 32, 34 and 36. In some embodiments, the purified polypeptide has a sequence selected from the group consisting of SEQ ID NO: 16, 18, 20, 22, 24, 26, 28, 30, 32, 34 and 36.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 16 shows the nucleic acid and amino acid sequences of the soybean genes described herein. The *A. thaliana* GRP7 sequences also are shown.

DETAILED DESCRIPTION

Figure 1:
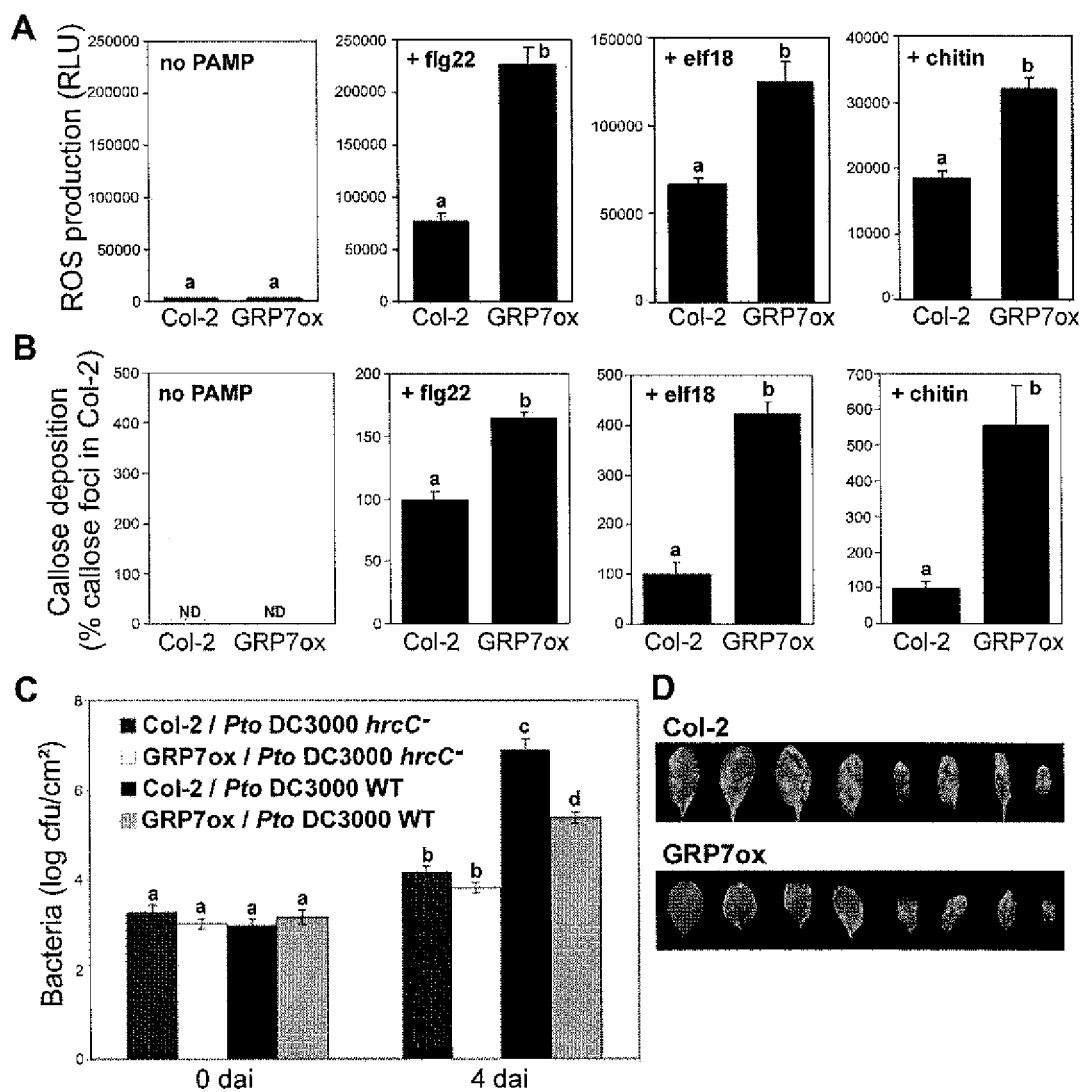
FIG. 1 shows that GRP7 overexpression enhances significantly PTI responses and resistance to Pseudomonas infection. Panel (A) shows the oxidative burst triggered by 1 μM flg22, 1 μM elf18, 100 μg/mL chitin or in the absence of PAMP treatment in Col-2 and transgenic *A. thaliana* plants overexpressing GRP7 (GRP7ox). ROS production is presented as total photon count during 25 min of treatment and measured in relative light units (RLU). Values are mean±SE (n=6). Statistical significance was assessed using the ANOVA test (P<0.001). Panel (B) shows callose deposition induced by 1 μM flg22, 1 μM elf18, 100 μg/mL chitin or in the absence of PAMP treatment, directly infiltrated in Col-2 and transgenic *A. thaliana* plants overexpressing GRP7 (GRP7ox). Values are mean±SE (n=24). Statistical significance was assessed using the ANOVA test (P<0.001). ND, non detectable. Panel (C) shows the growth of *Pseudomonas syringae* pv. tomato (Pto) DC3000 on Col-2 and GRP7ox plants as measured by colony forming units (cfu). Bacterial growth was measured four days after spray-inoculation with the wild-type strain (WT) or the hrcC$^+$ strain. Values are mean±SE (n=4). dai, days after-inoculation. Statistical significance was assessed using the ANOVA test (P<0.001). Panel (D) shows the disease symptoms on Col-2 and GRP7ox plants, four days after spray-infection with Pto DC3000 WT. All results shown are representative of at least three independent experiments.

HopU1, a mono-ADP-ribosyltransferase (ADP-RT) from the pathogen, *P. syringae*, modifies GRP7, an RNA-binding protein in the plant. Native GRP7 binds to FLS2 and EFR RNA, but this binding is reduced when GRP7 is ribosylated at Arg 49 (R49). In addition, plants lacking GRP7 indicate that GRP7 plays a role in innate immunity. See, for example, Fu et al., 2007, Nature, 447:284-8; and Jeong et al., 2011, J. Biol. Chem., 286:43272-81.

In order to increase the innate immunity of an agricultural crop, soybean sequences were identified that have a significant amount of homology to GRP7. These sequences were cloned and introduced into soybean plants, and their effect on innate immunity was evaluated. Innate immunity also is known as non-specific immunity and recognize and respond to pathogens immediately but does not confer long-lasting immunity to the host. Representative examples of biotic stresses include, without limitation, pathogens (e.g., bacteria, fungi, protozoa viruses, insects) or a physical lesion or wound.

Nucleic Acids and Polypeptides

The sequences identified in soybean have the nucleic acid sequences shown in SEQ ID NOs: 15, 17, 19, 21, 23, 25, 27, 29, 31, 33 and 35. The term "nucleic acid" refers to a deoxyribonucleic acid or a ribonucleic acid in single- or double-stranded form, sense or anti-sense, and, unless otherwise indicated, encompasses known analogues of natural nucleotides that hybridize to nucleic acids in a manner similar to naturally occurring nucleotides. Unless otherwise indicated, a particular nucleic acid sequence includes the complementary sequence thereof. The term "operably linked" refers to functional linkage between a nucleic acid expression control sequence (such as a promoter, signal sequence, or transcription factor binding sites) and a coding nucleic acid sequence, wherein the expression control sequence affects transcription and/or translation of the coding nucleic acid sequence.

Alignment of two or more sequences may be conducted, for example, using any number of methods (e.g., the local homology algorithm of Smith and Waterman (1981, Adv. Appl. Math. 2:482), the homology alignment algorithm of Needleman and Wunsch (1970, J. Mol. Biol. 48:443), the search for similarity method of Pearson and Lipman (1988, PNAS USA, 85:2444), computerized implementations of these algorithms (GAP, BESTFIT, FASTA, and TFASTA, as provided by, for example, the Wisconsin Genetics Software Package, Genetics Computer Group, Madison, Wis.) or inspection). The preferred method of alignment uses the Basic Local Alignment Search Tool (BLAST) (Altschul et al., 1990, J. Mol. Biol., 215:403-10) available from ncbi.nlm.nih.gov on the World Wide Web.

The term "percent sequence identity" as applied to an amino acid sequence refers to a polypeptide that has at least 70% sequence identity (e.g., at least 80%, 90%, 95%, 99% or 100% sequence identity) compared to another amino acid sequence (e.g., SEQ ID NO: 16, 18, 20, 22, 24, 26, 28, 30, 32, 34 or 36). The term "percent sequence identity" as applied to nucleic acid sequences refers to a nucleic acid sequence that has at least 50% sequence identity (e.g., at least 60%, 65%, 70%, 75%, 80%, 85%, 90%, 95%, 99%, or 100% sequence identity) relative to another nucleic acid sequence (e.g., SEQ ID NOs: 15, 17, 19, 21, 23, 25, 27, 29, 31, 33 or 35).

Another indication that nucleic acids possess sequence identity is if the two nucleic acid molecules hybridize to each other under stringent conditions. Stringent conditions are sequence-dependent and will be different in different circumstances. Generally, stringent conditions are selected to be about 5° C. to about 20° C. (e.g., about 10° C. to about 15° C.) lower than the thermal melting point (Tm) for the specific sequence (i.e., at a defined ionic strength and pH). The Tm is the temperature (i.e., under defined ionic strength and pH) at which 50% of a first nucleic acid sequence hybridizes to a second nucleic acid sequence. Typically, stringent conditions are those in which the salt concentration is about 0.02 M at pH 7 and the temperature is at least about 60° C. For example, stringent hybridization conditions can include an initial wash in 6×SSC at 42° C. followed by one or more additional washes in 0.2×SSC at a temperature of at least about 55° C. (e.g., about 60° C. or 65° C.).

A "purified polypeptide" refers to a polypeptide that has been separated from most components which naturally accompany it. Typically, a polypeptide is purified when it is at least 60%, by weight, free from the proteins and naturally-occurring organic molecules with which it is naturally associated (e.g., at least 75%, 80%, 85%, 90%, 95%, or 99%, by weight). Polypeptides may be obtained and purified using, for example, extraction from a natural source (for example, a plant cell); expression of a recombinant nucleic acid encoding the polypeptide; or chemically synthesizing the protein. Purity can be measured by any appropriate method, for example, column chromatography, polyacrylamide gel electrophoresis, or by HPLC analysis. Similarly, an "isolated nucleic acid" refers to a nucleic acid sequence free from the nucleic acid sequences that naturally flank it. Nucleic acids can be isolated using, for example, conventional molecular biology techniques including recombinant technologies.

Transgenic Soybean Plants and Methods of Making

Plant expression vectors typically include at least a cloned gene operably linked to regulatory sequences and a selectable marker. Regulatory sequences can include, without limitation, a promoter (for example, one conferring inducible or constitutive, pathogen- or wound-induced, environmentally- or developmentally-regulated, or cell- or tissue-specific expression), a transcription initiation start site, a ribosome binding site, an RNA processing signal, a transcription termination site, and/or a polyadenylation signal.

Representative promoters include a cauliflower mosaic virus (CaMV) promoter and a cassava vein mosaic virus (CsVMV) promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter. Other useful plant promoters include, without limitation, the nopaline synthase (NOS) promoter, the octopine synthase promoter, figwort mosaic virus (FMV) promoter, the rice actin promoter, and the ubiquitin promoter system.

A selectable marker is used to identify those cells or plants that contain and express the plant transformation vector. Selectable markers suitable for transgenic plants include the aminoglycoside phosphotransferase gene of transposon Tn5 (Aph II) and genes imparting antibiotic resistance (e.g., those encoding resistance to hygromycin, kanamycin, bleomycin, neomycin, G418, streptomycin, or spectinomycin). Selectable markers also include genes encoding herbicide resistance (e.g., the bar gene encoding phosphinothricin acetyltransferase, which confers resistance to the broad-spectrum herbicide, Basta) and other genes that impart herbicide resistance such as glyphosate.

Upon construction of the plant expression vector, several standard methods are available for introduction of the vector into a plant host, thereby generating a transgenic plant. These methods include Agrobacterium-mediated transformation (*A. tumefaciens* or *A. rhizogenes*) (see, for example, Lichtenstein and Fuller, In: Genetic Engineering, Vol 6, Rigby, ed., Academic Press, London, 1987; and Lichtenstein and Draper, In: DNA Cloning, Vol II, Glover, ed., IRI Press, Oxford, 1985; U.S. Pat. Nos. 4,693,976, 4,762,785, 4,940,838, 5,004,863, 5,104,310, 5,149,645, 5,159,135, 5,177,010, 5,231,019, 5,463,174, 5,469,976, and 5,464,763);

the particle delivery system (see, for example, U.S. Pat. Nos. 4,945,050 and 5,141,131);

microinjection protocols;

polyethylene glycol (PEG) procedures;

liposome-mediated DNA uptake;

electroporation protocols (see, for example, WO 87/06614 and U.S. Pat. Nos. 5,384,253, 5,472,869, 5,641,664, 5,679,558, 5,712,135, 6,002,070, and 6,074,877);

the vortexing method; or the "whiskers" methodology (see, for example, U.S. Pat. Nos. 5,302,523 and 5,464,765).

Plant cells (e.g., protoplasts), plant tissue (e.g., embryonic tissue, callus tissue type I and II, hypocotyls, meristem, and the like) or seeds can be transformed with a plant expression vector as described herein.

Once introduced into the plant cells, expression (e.g., of the selectable marker or of the gene to be expressed) may be assayed by any means known to the art, and expression may be measured as mRNA transcribed or protein synthesized. For example, expression of a nucleic acid sequence can be evaluated using Northern blot analysis (Ausubel et al., 2001, Current Protocols in Molecular Biology, John Wiley & Sons, NY, and Sambrook et al., 1998, Molecular Cloning: A Laboratory Manual, Cold Spring Harbor Laboratory, NY), reverse transcription PCR (rtPCR) including quantitative rtPCR (see, e.g., Kawasaki et al., in PCR Technology: Principles and Applications of DNA Amplification, Erlich, Ed., Stockton Press, 1989; Wang et al., in PCR Protocols: A Guide to Methods and Applications, Innis et al., Eds., Academic Press, 1990; and Freeman et al., 1999, Biotechniques 26:112-122 and 124-125). Additional well-known techniques for determining expression of a gene include in situ hybridization, and fluorescent in situ hybridization (see, e.g., Ausubel et al., Current Protocols in Molecular Biology, John Wiley & Sons, NY, 2001). Similarly, expression of a nucleic acid sequence can be measured at the level of protein production using standard protein analysis techniques including Bradford assays, spectrophotometric assays, and immunological detection techniques, such as Western blotting or immunoprecipitation with an antibody specific for the desirable polypeptide (Ausubel et al., Current Protocols in Molecular Biology, John Wiley & Sons, NY, 2001, and Sambrook et al., Molecular Cloning: A Laboratory Manual, Cold Spring Harbor Laboratory, NY, 1989).

Once plant cells expressing the desired level of a desirable gene product are obtained, plant tissues and whole plants can be regenerated therefrom using methods and techniques well-known in the art. The regenerated plants are then reproduced by conventional means and the introduced genes can be transferred to other strains and cultivars by conventional plant breeding techniques. For example, a transgenic soybean plant as described herein (i.e., expressing or over-expressing one or more of the soybean sequences described herein) can be crossed with a second soybean plant and progeny of the cross can be selected that express or over-express one or more of the soybean sequences described herein. In some embodiments, the progeny (i.e., the $F_1$ population) can be crossed and an $F_2$ population produced, or the $F_1$ progeny can be backcrossed with one of the parent lines to produce a $BC_1$ population. It would be understood that any number of plant crosses can be performed to produce populations including, without limitation, $F_3$, $BC_1F_2$, and $BC_1F_3$ populations.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Part A

Overexpression in *Arabidopsis*

Example 1

Plant Material

*Arabidopsis thaliana*, *Nicotiana benthamiana* and *Nicotiana tabacum* were grown at 20-21° C. with a 10 h-photoperiod in environmentally controlled chambers. *Arabidopsis* seedlings were grown on plates containing Murashige and Skoog (MS) medium (Duchefa) and 1% sucrose at 22° C. with a 16 h-photoperiod.

All experiments were performed in Col-0 background, except if indicated otherwise. The fls2 mutant used in this study is SALK_093905. The GRP7ox (Col-2/35S::GRP7), HopU1 (Col-0135S::HopU1-HA), GRP7-GFP (Col-0/35S::GRP7-GFP), GRP7-HA (grp7-1/GRP7p::GRP7-HA), GRP7(R49K)-HA [grp7-1/GRP7p::GRP7(R49K)-HA] were previously published (see, for example, Fu et al., 2007, Nature, 447:284-288; Jeong et al., 2011, J Biol Chem, 286:43272-43281; Streitner et al., 2008, Plant J., 56:239-50; and Kim et al., 2008, Plant J., 55:455-466). The GRP7-GFP/HopU1 line was obtained by crossing the GRP7-GFP and HopU1 lines.

The estradiol-inducible HopU1 line (ind_HopU1) was obtained by transforming Col-0 with the vector pLN604 (derived from pER8; see, for example Zuo et al., 2000, Plant J., 24:265-273) carrying HopU1-HA. The expression of HopU1 was induced by spraying 15 μM β-estradiol for 16-20 hours. The GRP8-HA (Col-0/35S::GRP8-HA) line was obtained by transforming Col-0 with the binary vector pPZP212 carrying GRP8-HA. Homozygous lines with a single transgene insertion were used for the experiments.

Example 2

PTI Assays

PAMP treatments (flg22 and elf18 peptides synthetized by Peptron, South Korea; shrimp chitin from SIGMA) were performed by syringe infiltration of plant leaves or by addition of the elicitor into the liquid media. Oxidative burst assays were performed on leaf disks incubated in a solution containing luminol and peroxidase as previously described (see, for example, Zipfel et al., 2004, Nature, 428:764-767). Callose deposition was observed after infiltration with a solution of 1 μM PAMP for 16 hours as previously described (see, for example, Hann et al., 2007, Plant J., 49:607-618). Callose deposits were quantified using PDQuest™ software (Bio-Rad).

Example 3

*Pseudomonas* Infection

Bacterial strains used in this study were *Pseudomonas syringae* pv. tomato (Pto) DC3000 wild-type (WT), Pto DC3000 ΔhopU1 and Pto DC3000 hrcC⁺. For bacterial enumeration assays, plants were sprayed with the strains WT (inoculum: $10^6$ cfu/mL), ΔhopU1 (inoculum: $10^8$ cfu/mL) and hrcC⁺ (inoculum: $10^8$ cfu/mL), in presence of 0.001% (v/v) Silwet L-77. Sprayed plants were then covered with a transparent plastic lid for the remaining of the experiment. For the other assays, bacteria were infiltrated into *Arabidopsis* leaves with the strains WT (inoculum: $5 \times 10^7$ cfu/mL), ΔhopU1 (inoculum: $10^8$ cfu/mL) and hrcC⁺ (inoculum: $10^8$ cfu/mL).

Example 4

Yeast Two-Hybrid

The coding region corresponding to the cytoplasmic part of EFR (EFRcyt) was cloned in the pLexA vector (Clontech). The recombinant pLexA-EFRcyt was used to screen a cDNA library prepared from infected *Arabidopsis* plants (van der Biezen et al., 2000, PNAS USA, 97:3747-52) according to the indications of the manufacturer. The coding region of GRP7 from nucleotide 67 to 528 (corresponding to the region of the GRP7 clone identified during the initial screen) was re-cloned in the pB42AD vector to re-test the interaction.

Example 5

Agrobacterium-Mediated Transient Expression for Co-Immunoprecipitation, Sub-Cellular Localization and Bimolecular Fluorescence Complementation Experiments For the co-immunoprecipitation and sub-cellular localization experiments, the following previously described constructs were used: 35S::GRP7-eGFP (Fu et al., 2007, Nature, 447:284-288), 35S::EFR-3xHA (Schwessinger et al., 2011, PLoS Genet., 7:e1002046), 35S::FLS2-3xmyc (Chinchilla et al., 2006, Plant Cell, 18:465-76), 35S::BAK1-HA (Schwessinger et al., 2011, PLoS Genet., 7:e1002046), 35S::FLS2-GFP-His (Schwessinger et al., 2011, PLoS Genet., 7:e1002046) and 35S::HopU1-HA (Fu et al., 2007, Nature, 447:284-288). The *Agrobacterium* strains GV3101 carrying the indicated constructs were syringe-infiltrated in *Nicotiana benthamiana* or *Nicotiana tabacum* leaves at $OD_{600}$=0.4-0.6 and samples were collected 2 days post-infiltration.

For the bimolecular fluorescence complementation assays, the coding regions of FLS2, EFR, GRP7 and HopU1 was cloned into the BiFC binary vectors, pAM-PAT-355, as previously described (Lefebvre et al., 2010, Proc Natl Acad Sci USA, 107:2343-2348). The *Agrobacterium* strain, GV3101, expressing the silencing suppressor P19 and carrying the indicated constructs were syringe-infiltrated in *Nicotiana benthamiana* leaves at $OD_{600}$=0.4-0.6.

Confocal analyses for the sub-cellular localization and bimolecular fluorescence complementation experiments were performed 2 days post-infiltration using a Leica SP5 confocal microscope.

Example 6

Protein Extraction, Co-Immunoprecipitation and Immunoblotting

Total proteins were extracted in a buffer including 100 mM Tris-HCl pH 7.5, 150 mM NaCl, 5 mM EDTA, 5% glycerol, 10 mM DTT, 0.5% Triton X-100, 1% Igepal and protease inhibitors (Sigma). For co-immunoprecipitation, anti-HA beads (Roche) or anti-GFP-TRAP-A beads (Chromotek) were incubated with total proteins and then washed with the extraction buffer. Proteins were fractioned on SDS-PAGE, transferred onto PVDF membranes (Bio-Rad) and then detected using specific antibodies. FLS2 was detected using specific polyclonal antibodies raised in rabbit as primary antisera. The anti-S14-1 antibodies were obtained from a commercial supplier (Agrisera, Sweden). The rabbit anti-eIF4E antibody was a kind gift from Prof. A. Maule (John Innes Centre, Norwich, UK). Epitope-tagged proteins were detected with a peroxidase-conjugated anti-HA-HRP (Santa Cruz); mouse monoclonal anti-GFP antibodies (AMS); or anti-HRP antibodies (Santa Cruz). The secondary anti-rabbit-HRP antibodies (Sigma) were used when appropriate. Immunodetection was performed with ECL chemiluminescence reagent (GE). Tandem mass spectrometry experiments were performed as previously described (Fu et al., 2007, Nature, 447:284-288).

Example 7

In Vitro ADP-Ribosylation Assay

HopU1-His, GRP7-GST and FLS2-GST were affinity-purified from *Escherichia coli* BL21 and the purity of the proteins was examined by SDS-PAGE. The ADP-ribosylation assay was performed as previously described (Fu et al., 2007, Nature, 447:284-288).

Example 8

RNA-Immunoprecipitation Assay

After UV-crosslinking treatments (120 MJ, 3 times using UV Stratalinker™ 2400, Stratagene), total proteins were extracted in extraction buffer including 50 mM Tris-HCl pH8, 150 mM NaCl, 2.5 mM EDTA, 10% glycerol, 10 mM PMSF, 10 units/mL RNaseOUT™ (Invitrogen) and protease inhibitors (Sigma). After centrifugation, the supernatant was incubated with anti-HA affinity matrix (Roche) or anti-GFP-TRAP-A beads (Chromotek). After this incubation, the beads were washed and the RNA-GRP7 complexes were eluted by incubating at 60° C. for 15 min in the elution buffer (1% SDS, 0.1 M NaHCO₃). A proteinase K treatment for 1 hour at 60° C. was then followed by RNA extraction and quantitative RT-PCR.

Figure 14:
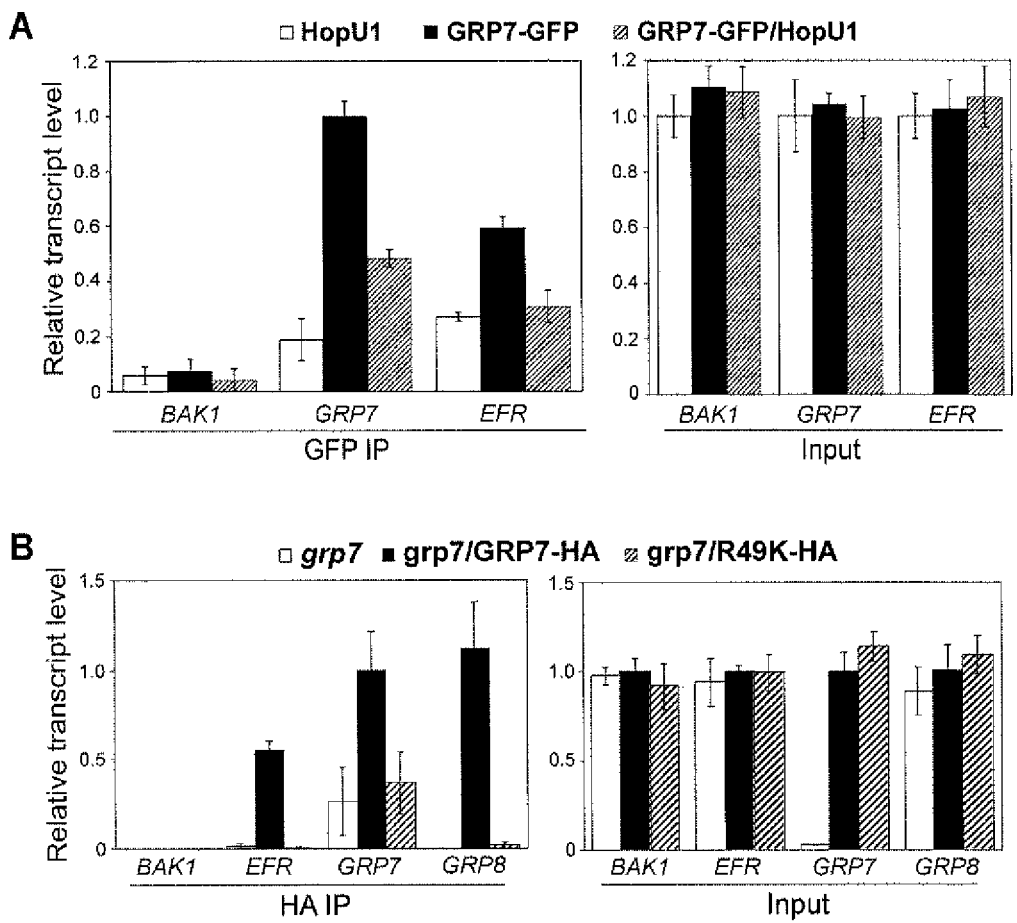
FIG. 14 shows that HopU1 disrupts GRP7-EFR transcript interactions. Panel (A) shows RNA immunoprecipitation in HopU1-HA, GRP7-GFP and GRP7-GFP/HopU1-HA A. thaliana lines. Total proteins were subjected to immunoprecipitation with GFP Trap beads followed by quantitative RT-PCR analysis of BAK1, EFR, and GRP7 transcripts with specific primers. Values are mean±SE (n=4). Panel (B) shows RNA immunoprecipitation in grp7, grp7/GRP7-HA and grp7/GRP7(R49K)-HA A. thaliana lines. Total proteins were subjected to immunoprecipitation with anti-HA matrix beads followed by quantitative RT-PCR analysis of BAK1, EFR, GRP7 and GRP8 transcripts with specific primers. Values are mean±SE (n=4).
Figure 15:
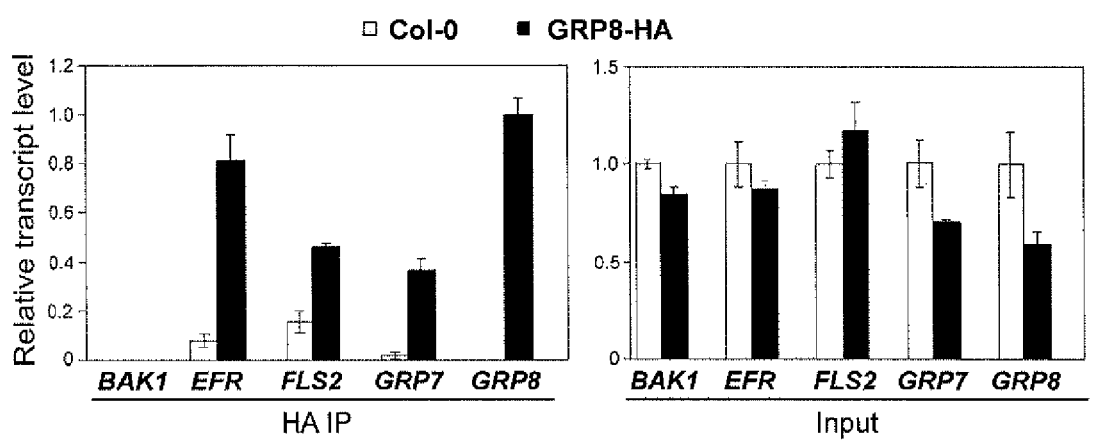
FIG. 15 shows that GRP8 binds FLS2 and EFR transcripts. RNA immunoprecipitation in Col-0 and GRP8-HA *A. thaliana* lines. Total proteins were subjected to immunoprecipitation with anti-HA beads followed by quantitative RT-PCR analysis of BAK1, EFR, FLS2, GRP7 and GRP8 transcripts with specific primers. Values are mean±SE (n=4).

In each experiment, transcript levels from the input were normalized in comparison to the control samples (grp7/GRP7-HA in FIGS. 1A, 6B and 14B; HopU1 in FIGS. 6A and 14A; and Col-0 in FIG. 15). The normalization of the transcript levels after RNA-IP was performed in comparison to the GRP7 transcript level in grp7/GRP7-HA or GRP7-GFP samples (FIGS. 5A, 6A-B, 14A-B) or the GRP8 transcript level (FIG. 15).

Example 9

Quantitative RT-PCR

After RNA extraction (Tri Reagent, Sigma-Aldrich), first strand cDNA was synthesized using the SuperScript II Reverse Transcriptase (Invitrogen). Quantitative PCRs were performed from 1.5 µL of cDNA with SYBR® Green Jump-Start™ Taq ReadyMix™ (Sigma-Aldrich) on a PTC-200 Peltier Thermal Cycler (MJ Research, Waltham, Mass.). Primers used have the following sequence:

```
Ubox (At5g15400):
                            (SEQ ID NOs: 1 & 2)
5'-TGCGCTGCCAGATAATACACTATT-3'
and

5'-TGCTGCCCAACATCAGGTT-3'

FLS2 (At5g46330):
                            (SEQ ID NOs: 3 & 4)
5'-ACTCTCCTCCAGGGGCTAAGGAT-3'
and

5'-AGCTAACAGCTCTCCAGGGATGG-3'

EFR (At5g20480):
                            (SEQ ID NOs: 5 & 6)
5'-CGGATGAAGCAGTACGAGAA-3'
and

5'-CCATTCCTGAGGAGAACTTTG-3'

BAK1 (At4g33430):
                            (SEQ ID NOs: 7 & 8)
5'-ACCGCCTCCTATCTCTCCTACACC-3'
and

5'-CTGGGTCCTCTTCAGCTGGTACA-3'

GRP7 (At2g21660):
                            (SEQ ID NOs: 9 & 10)
5'-TGATGACAGAGCTCTTGAGACTGCC-3'
and

5'-TCCTCCTCCACCCTCGCGTCTACCGCCGCCA-3'

GRP8 (At4g39260):
                            (SEQ ID NOs: 11 & 12)
5'-CAATGATGAAGATCTTCAAAGGACG-3'
and

5'-CTCGTAACCACCACCGCCTCCTCCTGAGTATCC-3'
```

Example 10

Electrophoretic Mobility Shift Assay

The 3'UTR sequence of FLS2 was amplified with the upstream primer GATGGTACCGAAGTTTAGCAG-CAAAGC (SEQ ID NO:13) and the downstream primer GAGCTCGAGGTTCATCAAAACCAAATTTC (SEQ ID NO:14). The amplified fragment was subcloned into the plasmid pBSK(−) (Stratagene) and transcribed with T7 polymerase (Promega) in the presence of 10 µCi $^{32}$P CTP. The FLS2 3'UTR binding affinity was analyzed with purified GRP7-GST in 20 mM HEPES, pH7.5, 100 mM NaCl, 1 mM MgCl2, 0.01% NP-40, 10 U SUPERase•In™ (Ambion), and 50 ng of $^{32}$P-labeled FLS2 3'UTR. For competition assays, unlabelled FLS2 3'UTR transcripts were added into the mixture of 2 mM GRP7-GST and 50 ng of $^{32}$P-labelled FLS2 3-UTR transcripts. The bound and free RNA probes were separated on 6% native PAGE and exposed to PhotoImage screen, then analyzed by Storm 860 scanner (Molecular Dynamics).

Example 11

Statistical Analysis

Statistical significances based on one-way ANOVA analyses were performed with Prism 5.01 software (GraphPad Software).

Example 12

Modulation of GRP7 Level and Activity Affects Early and Late Immune Responses

Figure 8:
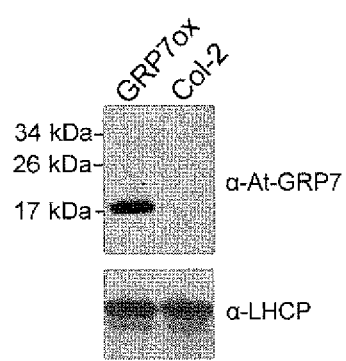
FIG. 8 shows GRP7 over-expression in the GRP7ox line. Immunoblots with a specific antibody detecting GRP7 in Col-2 and the transgenic Arabidopsis thaliana line overexpressing GRP7 (GRP7ox). The blot obtained with the antibody anti-LHCP (Light Harvesting Chlorophyll a/b Protein) served as a loading control.

Previous results conclusively showed that loss of GRP7 impairs PTI and resistance to Pto DC3000 infection. To investigate the consequences of ectopic GRP7 expression, PTI and pathogen response was monitored in transgenic *A. thaliana* plants expressing untagged GRP7 under the control of the constitutive promoter 35S (GRP7ox lines; Streitner et al., 2008, Plant J., 56:239-50). An immunoblot analysis using a specific anti-GRP7 antibody confirmed higher GRP7 levels in transgenic homozygous GRP7ox plants in comparison to the wild-type (WT) Col-2 ecotype (FIG. 8). *A. thaliana* Col-2 (WT) and GRP7ox plants were treated with flg22, elf18, or chitin, which resulted in substantially higher ROS production in GRP7ox plants compared to WT (FIG. 1A). Similarly, callose deposition was increased in GRP7ox plants compared to WT plants after all three treatments (FIG. 1B).

The *A. thaliana* GRP7ox plants were used in pathogenicity assays with Pto DC3000 or the Pto DC3000 hrcC$^+$ mutant that does not secrete any T3SEs and is therefore severely hypovirulent. Plants were spray-inoculated and bacteria were enumerated at 0 and 4 days after inoculation. Interestingly, GRP7ox plants were more resistant to infection by Pto DC3000 than WT plants (FIGS. 1C and D). The Pto DC3000 hrcC$^+$ mutant exhibited unaltered growth on GRP7ox plants. This may be due to the strongly reduced virulence of the Pto DC3000 hrcC$^+$ mutant that would require a more substantial improvement in plant immunity to further reduce the growth of this debilitated strain. The increased resistance to Pto DC3000 infection observed in plants over-expressing GRP7 clearly demonstrates its important role in innate immunity.

Example 13

GRP7 is Required for Full Immunity to Pto DC3000 Wt and HrcC$^+$, and HopU1 Targets GRP7

Figure 9:
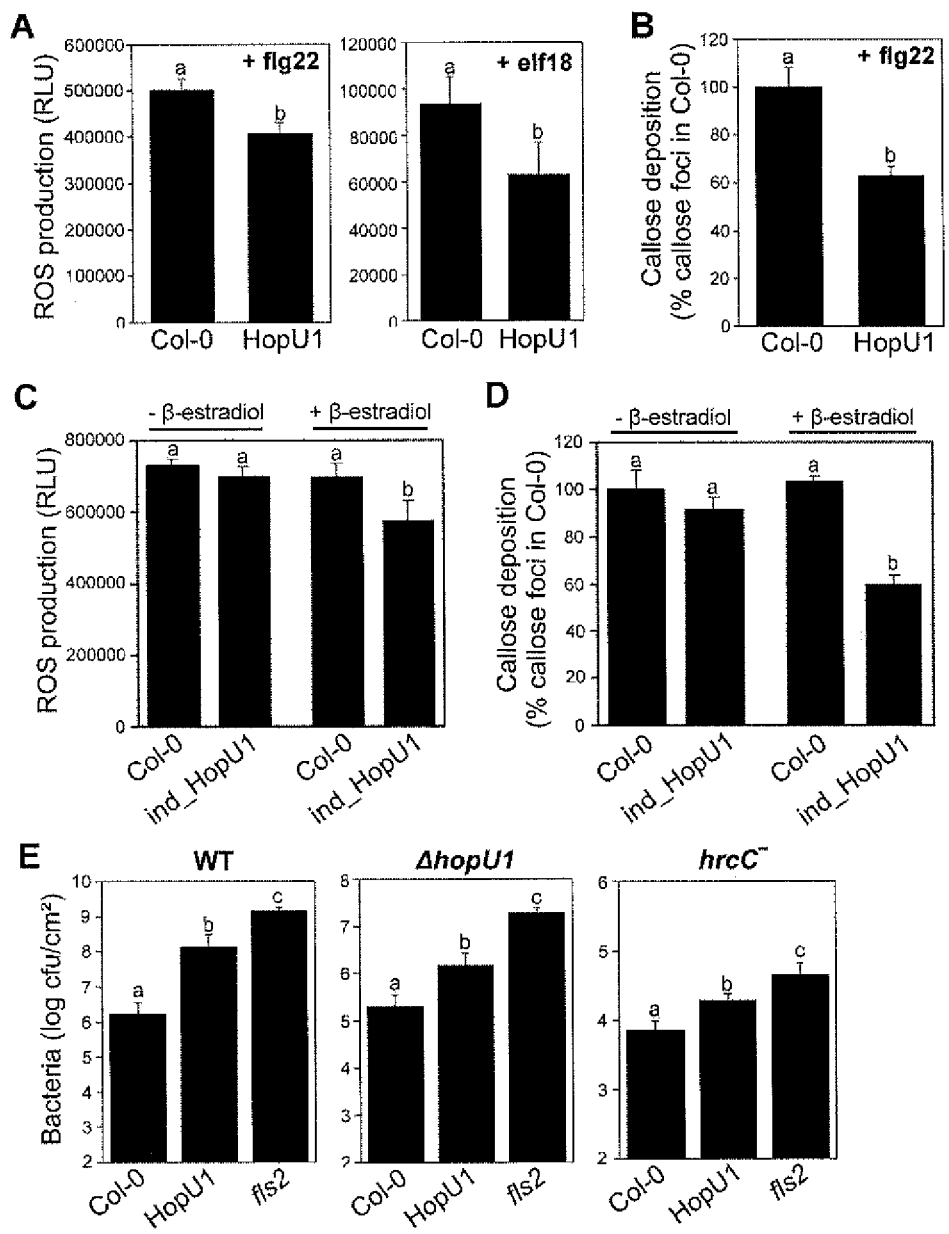
FIG. 9 shows that HopU1 suppresses early and late immune responses triggered by flg22 in Arabidopsis. Panel (A) shows the oxidative burst triggered by 50 nM flg22 or 50 nM elf18 in Col-0 and transgenic A. thaliana plants expressing HopU1-HA under 35S promoter (HopU1). ROS production is presented as total photon count during 40 min of treatment and measured in relative light units (RLU). Values are mean±SE (n=12). Statistical significance was assessed using the ANOVA test (P<0.001). Panel (B) shows callose deposition induced by 1 μM flg22 infiltrated in Col-0 and transgenic A. thaliana plants expressing HopU1-HA under 35S promoter (HopU1). Values are mean±SE (n=10). Statistical significance was assessed using the ANOVA test (P<0.001). Panel (C) shows the oxidative burst triggered by 50 nM flg22 in Col-0 and transgenic A. thaliana plants expressing HopU1-HA under the control of an estradiol-inducible promoter (ind_HopU1), with or without a 15 μM β-estradiol pre-treatment. ROS production is presented as total photon count during 40 min of treatment and measured in relative light units (RLU). Values are mean±SE (n=12). Statistical significance was assessed using the ANOVA test (P<0.001). Panel (D) shows callose deposition induced by 1 μM flg22 infiltrated in Col-0 and transgenic A. thaliana plants expressing HopU1-HA under the control of an estradiol-inducible promoter (ind_HopU1), with or without a 15 μM β-estradiol pre-treatment. Values are mean±SE (n=10). Statistical significance was assessed using the ANOVA test (P<0.001). Panel (E) shows the growth of Pseudomonas syringae pv. tomato (Pto) DC3000 on Col-0, HopU1 (35S::HopU1-HA) and fls2 plants as measured by colony forming units (cfu). Bacterial growth was measured three days after spray-inoculation with wild-type Pto DC3000 (WT; inoculum: $10^6$ cfu/mL), Pto DC3000 ΔhopU1 (inoculum: $10^8$ cfu/mL) and Pto DC3000 hrcC$^+$ (inoculum: $10^8$ cfu/mL). Values are mean±SE (n=4). Statistical significance was assessed using the ANOVA test (P<0.05). All results shown are representative of at least three independent experiments.

To assess the extent to which HopU1 inhibits PTI responses, early and late responses triggered by flg22 were analyzed in transgenic *A. thaliana* lines constitutively expressing HopU1 C-terminally tagged with hemagglutinin (HA) under the control of the 35S promoter. In HopU1 plants, the ROS burst induced by flg22 and elf18 treatment was reduced compared to WT plants (FIGS. 9A and B). Next, it was confirmed that HopU1 leaves exhibit less callose deposition upon flg22 treatment (FIG. 9C). These results were further validated using *A. thaliana* transgenic lines expressing HopU1-HA under the control of an estradiol-inducible promoter (ind_HopU1) (FIGS. 9D and E). Together, this demonstrates that HopU1 affects both early and late flg22-induced responses.

To test whether in planta HopU1 expression affects *A. thaliana* disease resistance, bacterial growth was assayed after spray-inoculation with the Pto DC3000 strains WT, hrcC$^+$, or ΔhopU1 that is hypo-virulent. HopU1 plants were more susceptible to all the strains tested (FIG. 9F), albeit to a lesser extent than fls2 null mutant plants consistent with the reduced flg22 sensitivity of HopU1 plants (FIGS. 9A and C-E). These results, together with previous results, indicate that the abundance and/or activity of GRP7 are both required and limiting for triggering optimal early and late PTI responses.

Example 14

GRP7 Associates with the Immune Receptors FLS2 and EFR at the Plasma Membrane

The importance of GRP7 for early PTI responses suggests that GRP7 may affect directly PRRs and/or associated proteins, or indirectly the expression and/or biogenesis of such proteins.

Figure 10:
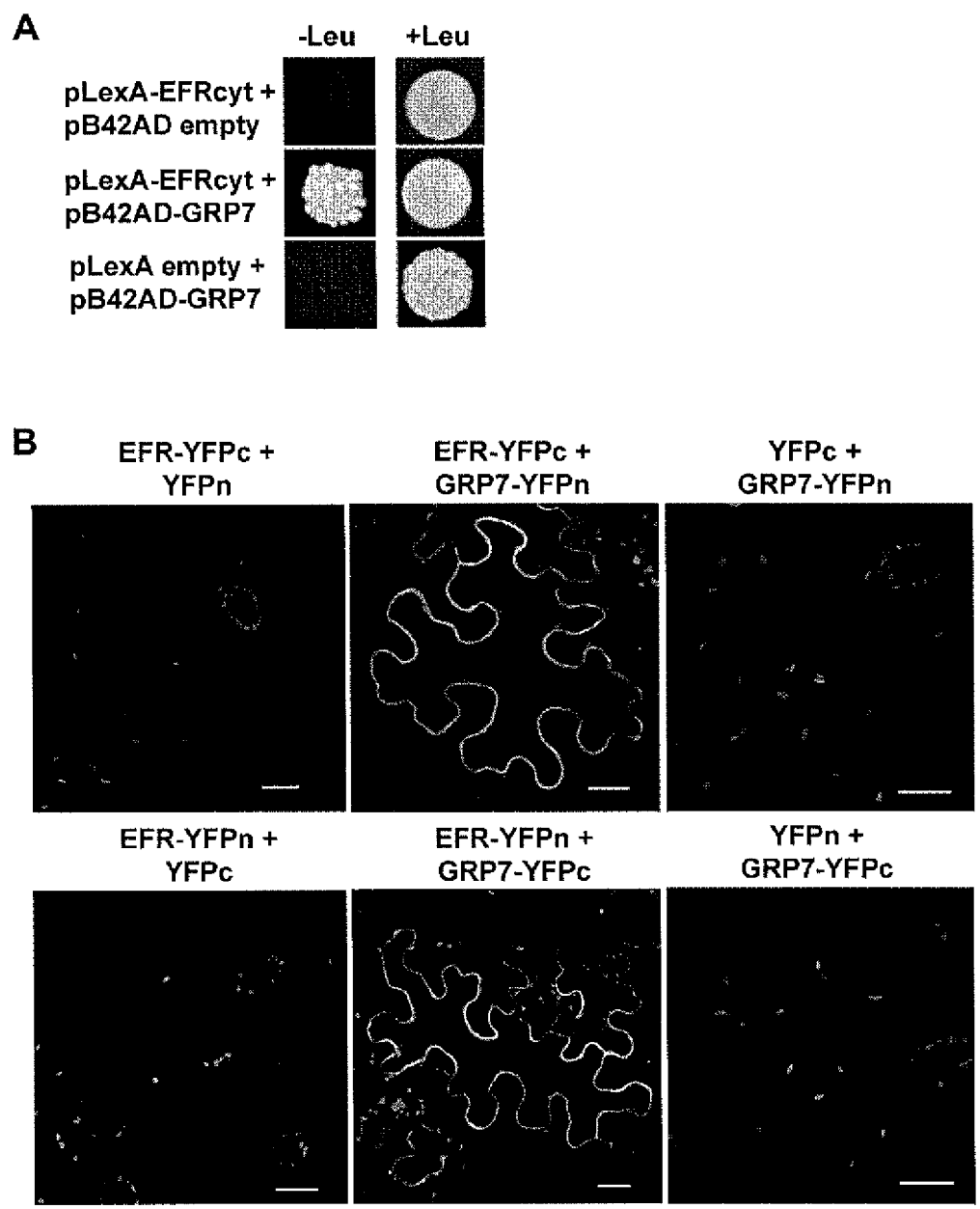
FIG. 10 shows that GRP7 interacts with EFR at the plasma membrane. Panel (A) shows that EFR and GRP7 interact in yeast two-hybrid assays. The cytoplasmic part of EFR (EFR-cyt) has been found to interact with GRP7 during a yeast two-hybrid screen and confirmed upon expression of pLexA-EFRcyt and pB42AD-GRP7. Interaction assays were performed in presence or absence of the auxotrophic amino acid leucine (Leu). Panel (B) shows the bimolecular fluorescence complementation assays between GRP7 and EFR. YFPn, GRP7-YFPn, YFPc and EFR-YFPc, as well as the reverse combinations YFPc, GRP7-YFPc, YFPn and EFR-YFPn, were transiently co-expressed in N. benthamiana leaves. Scale bar corresponds to 20 μm. Photographs were taken 2 days after infiltration and are representative of the total observations (n=60). All results shown are representative of three independent experiments.

Notably, GRP7 was identified in an unbiased yeast two-hybrid screen for EFR-interacting proteins (FIG. 10A). Importantly, this interaction was confirmed in co-immunoprecipitation experiments after transient co-expression of EFR and GRP7 as C-terminally tagged fusion proteins with HA and enhanced green fluorescent protein (GFP) tags (EFR-3xHA and GRP7-eGFP, respectively) in *Nicotiana benthamiana* (FIG. 2A). Similarly, GRP7 and FLS2 also interacted when transiently co-expressed as fusion proteins (FLS2-3xmyc and GRP7-eGFP) in *N. benthamiana* (FIG. 2B). However, GRP7-eGFP did not interact under similar conditions with the LRR-RK BAK1 (BAK1-HA) (FIG. 2C), which is an important positive regulator of PTI responses downstream of FLS2 and EFR.

The GRP7-FLS2 association was confirmed by co-immunoprecipitation in an *A. thaliana* transgenic line expressing GRP7 C-terminally tagged with a GFP epitope (GRP7-GFP) under the control of the 35S promoter and using an anti-FLS2 antibody recognizing the native FLS2 protein (FIG. 2D). The GRP7-FLS2 interaction occurred independently of elicitation and was unaltered by flg22 treatment (FIG. 2D). The presence of fully glycosylated EFR and FLS2 proteins (migrating at ~150 kDa and ~175 kDa, respectively) in the GRP7 immunoprecipitates (FIGS. 2A, B and D) suggests that the association between GRP7 and PRRs occurs at the plasma membrane once the mature and functional PRRs have migrated through the secretory pathway.

Figure 11:
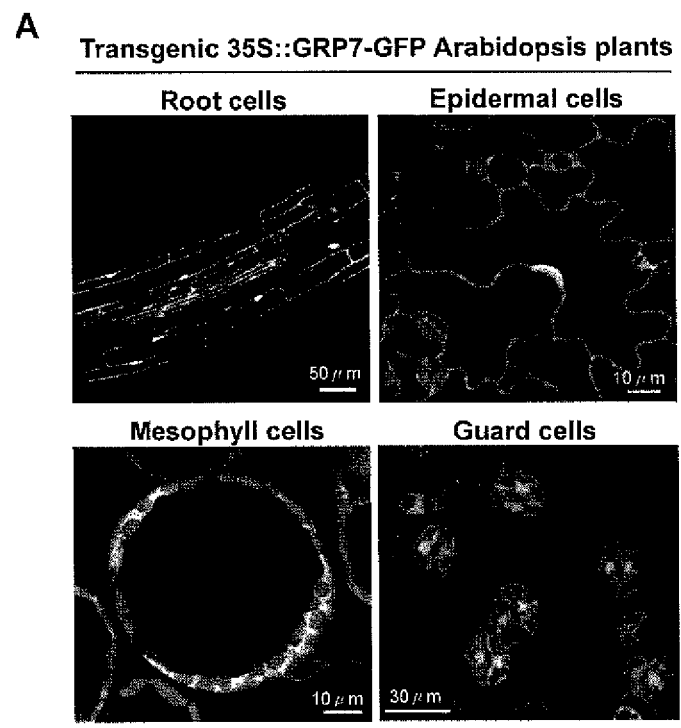
FIG. 11 shows GRP7 sub-cellular localization. Panel (A) shows GRP7 sub-cellular localisation in the stable transgenic on A. thaliana plants 35S::GRP7-GFP line as observed by confocal microscopy. Panel (B) shows the localization of GRP7-eGFP transiently expressed in N. benthamiana and N. tabacum as observed by confocal microscopy.
Figure 11:
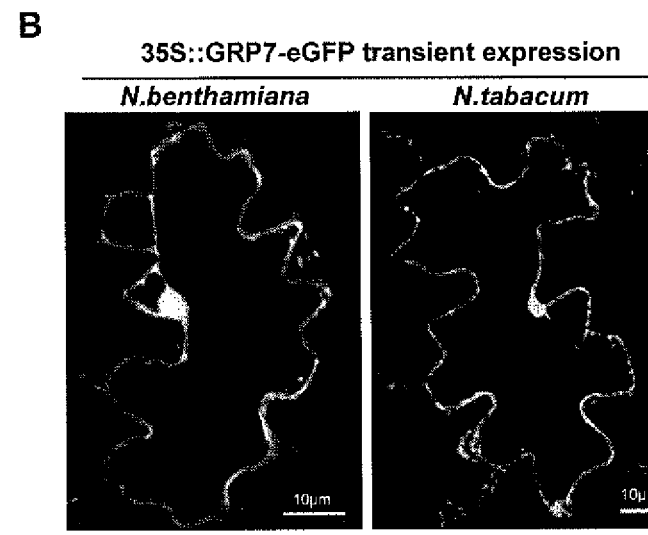

GRP7-GFP shows a nucleo-cytoplasmic subcellular localization in *A. thaliana*, tobacco (*Nicotiana tabacum*) and *N. benthamiana* cells upon stable or transient expression (FIGS. 11A and B). Bimolecular fluorescence complementation (BiFC) experiments using split-yellow fluorescent protein (YFP) following transient expression in *N. benthamiana* suggest that the GRP7-FLS2 interaction is direct (FIG. 2E). This interaction occurs most likely at the plasma membrane, as indicated by the presence of the reconstituted YFP signal in typical cell wall-plasma membrane connections (called Hechtian strands) after cell plasmolysis (arrows in FIG. 2E). An interaction at the plasma membrane between GRP7 and EFR could also be observed (FIG. 10B).

Example 15

GRP7 Associates with Translational Components

In exploratory experiments to identify GRP7 interactors in planta by immunoprecipitation using an *A. thaliana* transgenic line expressing GRP7 C-terminally tagged with HA under the control of its native promoter (GRP7-HA), several components of the 43S complex involved in protein translation were identified by mass-spectrometry analysis of the GRP7-HA immunoprecipitates (Table 8). Before the initiation of active translation, the 43S complex recruits both mRNAs and ribosomes, and is composed of several initiation factors in addition to the cap-binding protein eIF4E and the ribosomal 40S subunit.

Figure 2:
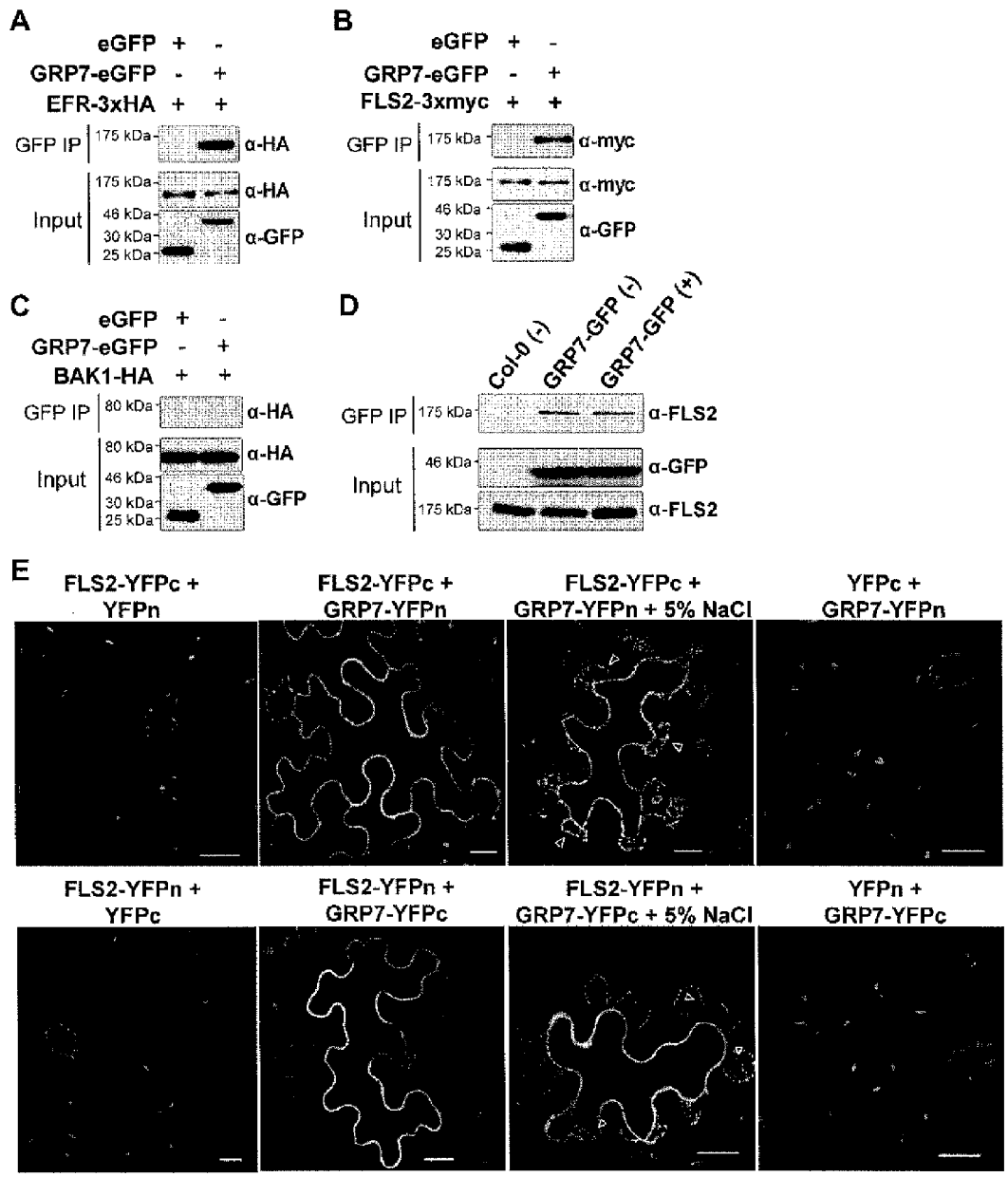
FIG. 2 shows that GRP7 associates with FLS2 at the plasma membrane. Panels (A-C) shows the co-immunoprecipitation assay performed after transient co-expression of GRP7-eGFP or eGFP with EFR-3xHA (A), FLS2-3xmyc (B) or BAK1-HA (C) in *N. benthamiana* plants. Total proteins (input) were subjected to immunoprecipitation with GFP Trap beads followed by immunoblot analysis. Panel (D) shows the co-immunoprecipitation of GRP7 and FLS2 in *A. thaliana*. Co-immunoprecipitation assay performed on Col-0 and GRP7-GFP plants untreated (−) or treated (+) with 1 μM flg22 for 15 min. Total proteins (input) were subjected to immunoprecipitation with GFP Trap beads followed by immunoblot analysis. Panel (E) shows the bimolecular fluorescence complementation assays between GRP7 and FLS2. YFPn, GRP7-YFPn, YFPc and FLS2-YFPc, as well as the reverse combinations YFPc, GRP7-YFPc, YFPn and FLS2-YFPn, were transiently co-expressed in *N. benthamiana* leaves. Plasmolysis experiment was performed in the presence of 5% NaCl for 5 min. Arrows indicate Hechtian strands. Scale bar corresponds to 20 μm. Photographs were taken 2 days after infiltration and are representative of the total observations (n=60). All results shown are representative of three independent experiments.
Figure 3:
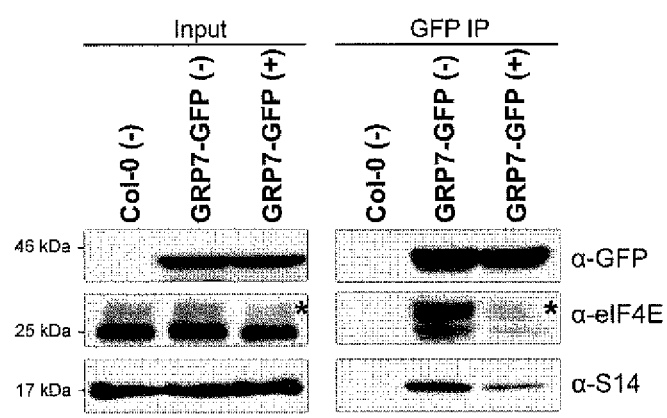
FIG. 3 shows that GRP7 associates with translational components in *Arabidopsis*. Co-immunoprecipitation assay performed on Col-0 and GRP7-GFP plants untreated (−) or treated (+) with 1 μM flg22 for 15 min. Total proteins (input) were subjected to immunoprecipitation with GFP Trap beads followed by immunoblot analysis with anti-GFP antibodies to detect GRP7-GFP or specific antibodies recognizing the translation initiation factor eIF4E and the ribosomal protein S14. Asterisks mark eIF4E slower-migrating bands. The results shown are representative of three independent experiments.

Co-immunoprecipitation experiments using the *A. thaliana* GRP7-GFP transgenic line and specific antibodies further revealed the presence of eIF4E and the ribosomal subunit S14 in complex with GRP7 (FIG. 3). The GRP7-GFP line was used here for consistency with previous targeted co-immunoprecipitation experiments (FIG. 2). Interestingly, slower-migrating bands of eIF4E were enriched in GRP7-GFP immunoprecipitates in comparison to the main form detected in the input (see asterisks in FIG. 3). Strikingly, treatment with flg22 induced the dissociation of eIF4E and S14 from the GRP7 complex (FIG. 3), indicating a potential dynamic link between GRP7, ligand-activated PRRs and components of the translational machinery.

Example 16

Figure 12:
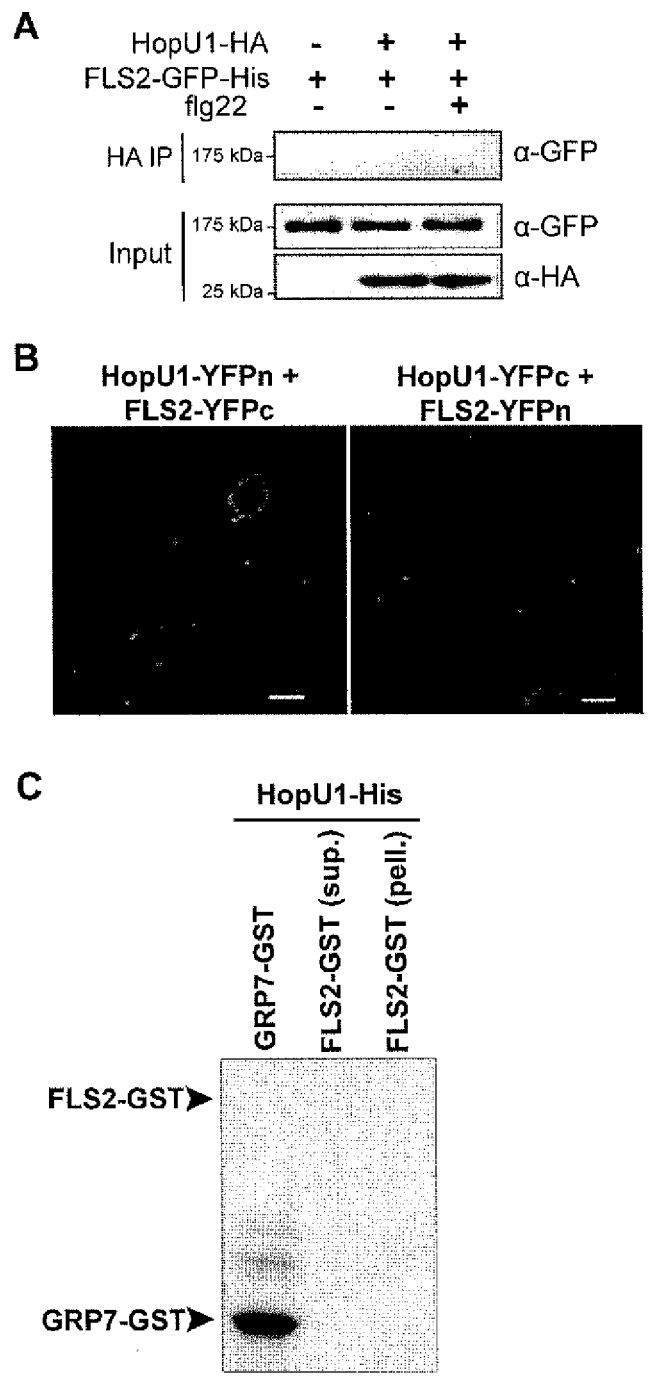
FIG. 12 shows that HopU1 does not interact with, nor ADP-ribosylates, FLS2 protein. Panel (A) shows the co-immunoprecipitation assay performed after transient co-expression of HopU1-HA and FLS2-GFP-His on N. benthamiana plants, with (+) or without (−) treatment of the samples with 1 μM flg22 for 15 min. Total proteins (input) were subjected to immunoprecipitation with anti-HA beads followed by immunoblot analysis. Panel (B) shows the bimolecular fluorescence complementation assays between HopU1 and FLS2. HopU1-YFPn and FLS2-YFPc, as well as the opposite combination HopU1-YFPc and FLS2-YFPn, were transiently co-expressed N. benthamiana leaves. Scale bar corresponds to 20 μm. Photographs were taken 2 days after infiltration and are representative of the total observations (n=60). Panel (C) shows the in vitro ADP-ribosylation assay performed with recombinant FLS2-GST and HopU1-His on supernatant (sup) and pellet (pell) fractions. The reaction between GRP7-GST and HopU1-His has been included as a positive control. All results shown are representative of three independent experiments.

HopU1 Does Not Affect Interactions Between GRP7, PRRs and Translational Components Next, it was tested whether HopU1 could directly affect FLS2 or the GRP7-FLS2 interaction. HopU1 did not interact with FLS2 in vivo as determined by co-immunoprecipitation and split-YFP experiments in *N. benthamiana* (FIG. 12A, B). Consistently, HopU1 did not mono-ADP-ribosylate FLS2 in vitro (FIG. 12C).

Figure 4:
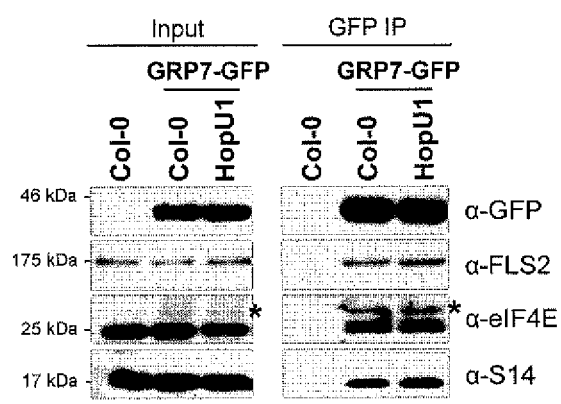
FIG. 4 shows that HopU1 does not affect the protein-protein interactions between GRP7, FLS2 and translational components. Co-immunoprecipitation assay performed on Col-0 and HopU1 *Arabidopsis* plants expressing or not GRP7-GFP. Total proteins (input) were subjected to immunoprecipitation with GFP Trap beads followed by immunoblot analysis with anti-GFP antibodies to detect GRP7 or specific antibodies recognizing FLS2, the translation initiation factor eIF4E, or the ribosomal protein S14. Asterisks mark slower-migrating bands forms. The results shown are representative of three independent experiments.
Figure 13:
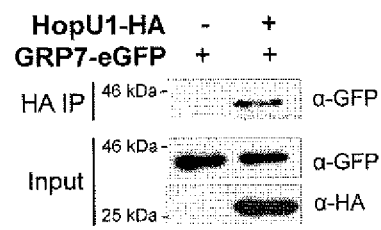
FIG. 13 shows that GRP7 interacts with HopU1 in the cytoplasm and in the nucleus. Panel (A) shows the co-immunoprecipitation of GRP7 and HopU1. GRP7-eGFP and HopU1-HA were transiently co-expressed in N. benthamiana leaves. Total proteins (input) were subjected to immunoprecipitation with anti-HA beads followed by immunoblot analysis with anti-GFP antibodies to detect GRP7-eGFP. Panel (B) shows the bimolecular fluorescence complementation assays between GRP7 and HopU1. GRP7-YFPn/c and HopU1-YFPc/n were transiently co-expressed in N. benthamiana leaves. Scale bar corresponds to 20 μm. Photographs were taken 2 days after infiltration and are representative of the total observations (n=60). All results shown are representative of three independent experiments.
Figure 13:
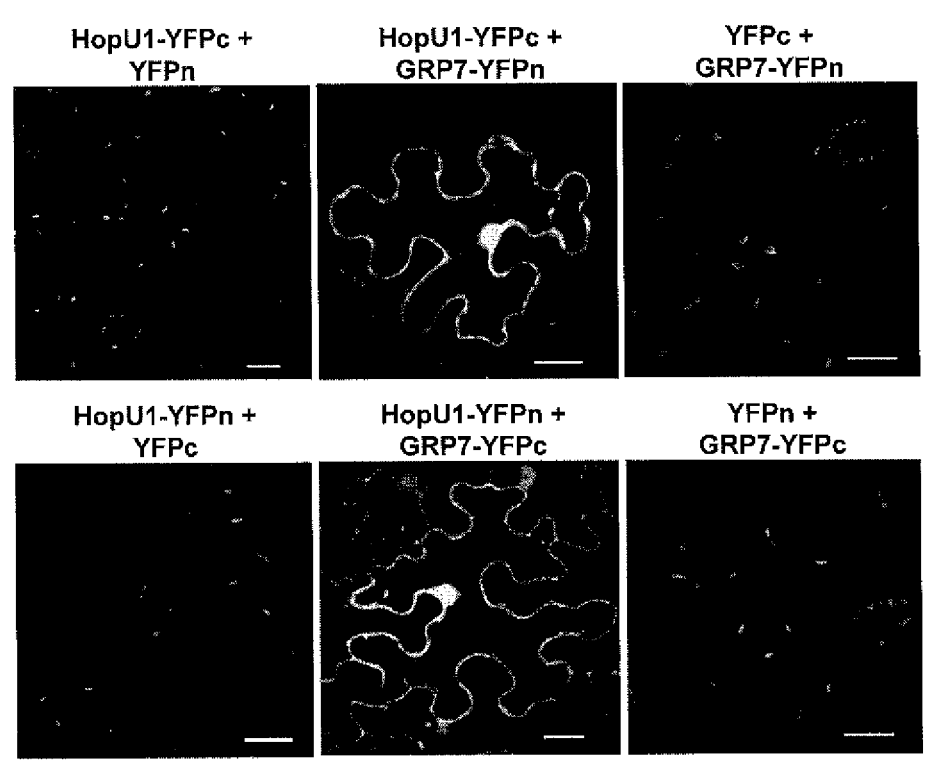

Although HopU1 directly interacts with GRP7 in vivo (FIG. 13), HopU1 did not affect the interaction between GRP7 and FLS2 in an *A. thaliana* transgenic line expressing both GRP7-GFP and HopU1-HA (FIG. 4). In addition, HopU1 did not interfere with the association between GRP7-GFP and either eIF4E or S14 (FIG. 4). Therefore, the effect of HopU1 on PTI responses is most likely not mediated by direct inhibition of PRRs or protein-protein interactions with GRP7.

Example 17

GRP7 Associates with FLS2 and EFR Transcripts in Planta

Figure 5:
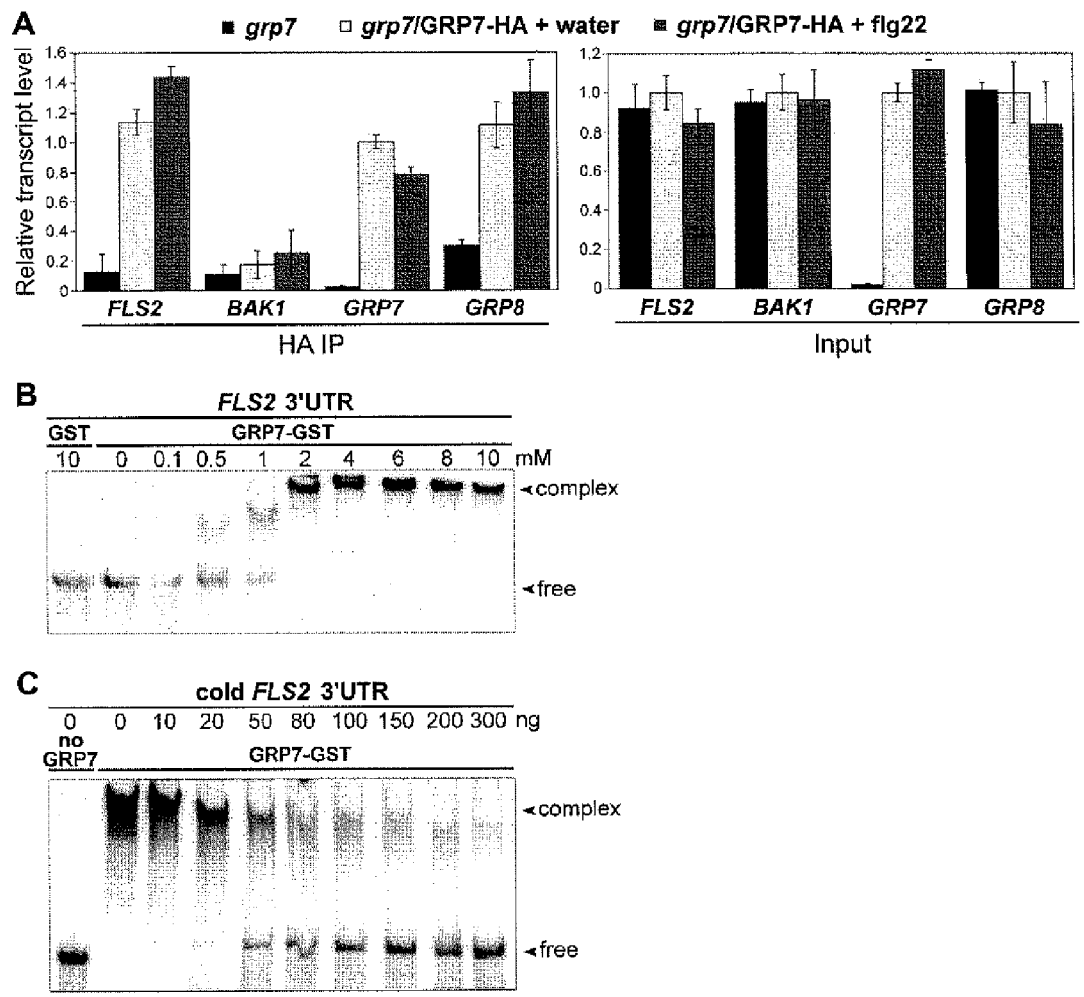
FIG. 5 shows that GRP7 binds FLS2 transcript. Panel (A) shows RNA immunoprecipitation in grp7-1 and grp7-1/GRP7-HA *A. thaliana* lines treated for 30 min with water or 1 μM flg22. Total proteins were subjected to immunoprecipitation with anti-HA antibodies followed by quantitative RT-PCR analysis of FLS2, BAK1, GRP7 and GRP8 transcripts with specific primers. Values are mean±SE (n=4). The results shown are representative of three independent experiments. Panels (B) and (C) show that GRP7 binds the 3'UTR of FLS2 transcripts in vitro. Electrophoretic shift assays performed on the 3'UTR of FLS2 RNAs, in presence of increasing concentrations of GRP7-GST (B). Competition assay were performed with increasing quantity of unlabeled FLS2 3'UTR transcripts to GRP7-GST and $^{32}$P-labeled FLS2 3'UTR transcripts (C). The results shown are representative of three independent experiments.
Figure 6:
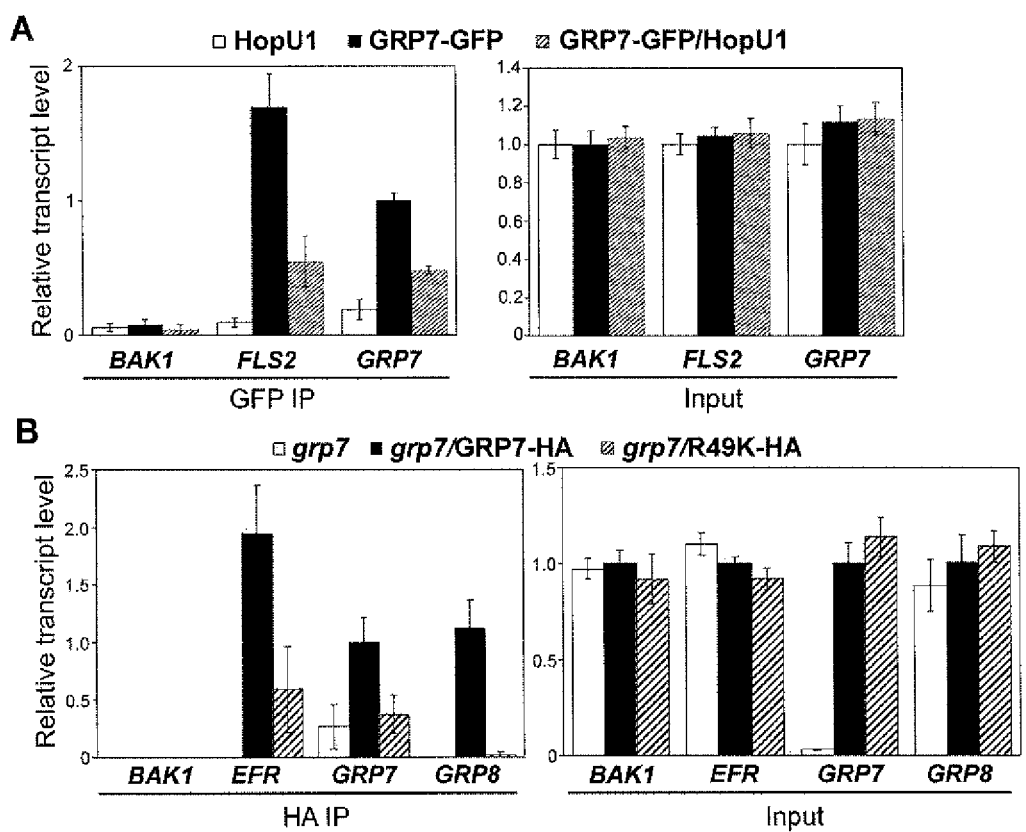
FIG. 6 shows that HopU1 disrupts GRP7-FLS2 transcripts interactions. Panel (A) shows RNA immunoprecipitation in HopU1, GRP7-GFP and GRP7-GFP/HopU1 *A. thaliana* lines. Total proteins were subjected to immunoprecipitation with GFP Trap beads followed by quantitative RT-PCR analysis of BAK1, FLS2 and GRP7 transcripts with specific primers. Values are mean±SE (n=4). Panel (B) shows RNA immunoprecipitation in grp7, grp7/GRP7-HA and grp7/GRP7 (R49K)-HA *A. thaliana* lines. Total proteins were subjected to immunoprecipitation with anti-HA matrix beads followed by quantitative RT-PCR analysis of BAK1, FLS2, GRP7 and GRP8 transcripts with specific primers. Values are mean±SE (n=4). The results shown are representative of three independent experiments.

Next, the role of GRP7 in PTI was investigated in relation to its capacity to bind RNA by testing if GRP7 could bind PRR transcripts. Quantitative RNA-immunoprecipitation assays using the *A. thaliana* GRP7-HA transgenic line revealed that GRP7 binds FLS2 mRNAs in vivo independently of flg22 treatment (FIG. 5A). As positive controls, it was confirmed that GRP7 binds its own transcripts as well as transcripts of its closest paralog GRP8 (FIG. 5A), as previously reported in vitro. GRP7 binds the 3'-UTR of its own transcript and of the GRP8 mRNA. Similarly, the 3'-UTR was identified as a binding region of GRP7 in the FLS2 mRNA (FIG. 5B, C). In addition to the FLS2 mRNA, GRP7 could also bind the EFR transcript in vivo (FIG. 14A), consistent with the importance of GRP7 for responses triggered by both flg22 and elf18 (FIG. 1). However, transcripts of the regulatory LRR-RK BAK1 were not enriched in GRP7 immunoprecipitates (FIGS. 5A and 14A), revealing a certain degree of specificity. Interestingly, GRP8, which is also targeted by HopU1, is also able to bind FLS2 and EFR mRNAs (FIG. 15). These results demonstrate that GRP7, as well as GRP8, bind transcripts of the important PRRs FLS2 and EFR.

Example 18

HopU1 Disrupts the Association Between GRP7 and PRR Transcripts

Next, it was investigated whether HopU1 could affect the ability of GRP7 to bind its target mRNAs, including FLS2 and EFR transcripts. Using an *A. thaliana* transgenic line expressing both GRP7-GFP and HopU1-HA in quantitative RNA-immunoprecipitation assays, it was found that the amount of FLS2 and EFR transcripts bound to GRP7-GFP was strongly reduced in the presence of HopU1 (FIGS. 6A and 14A). A similar effect was observed on the interaction between GRP7 and its own mRNA (FIGS. 6A and 14A). Furthermore, a GRP7(R49K) variant, which carries a mutation in a conserved arginine residue within the RRM RNA-binding domain that is mono-ADP-ribosylated by HopU1, is strongly impaired in its ability to bind FLS2, EFR, GRP7 and GRP8 transcripts (FIGS. 6B and 14B). Together, these results demonstrate that the mono-ADP-ribosylation of GRP7 by HopU1 disrupts in planta the ability of GRP7 to bind mRNAs of the PRRs FLS2 and EFR.

Example 19

Figure 7:
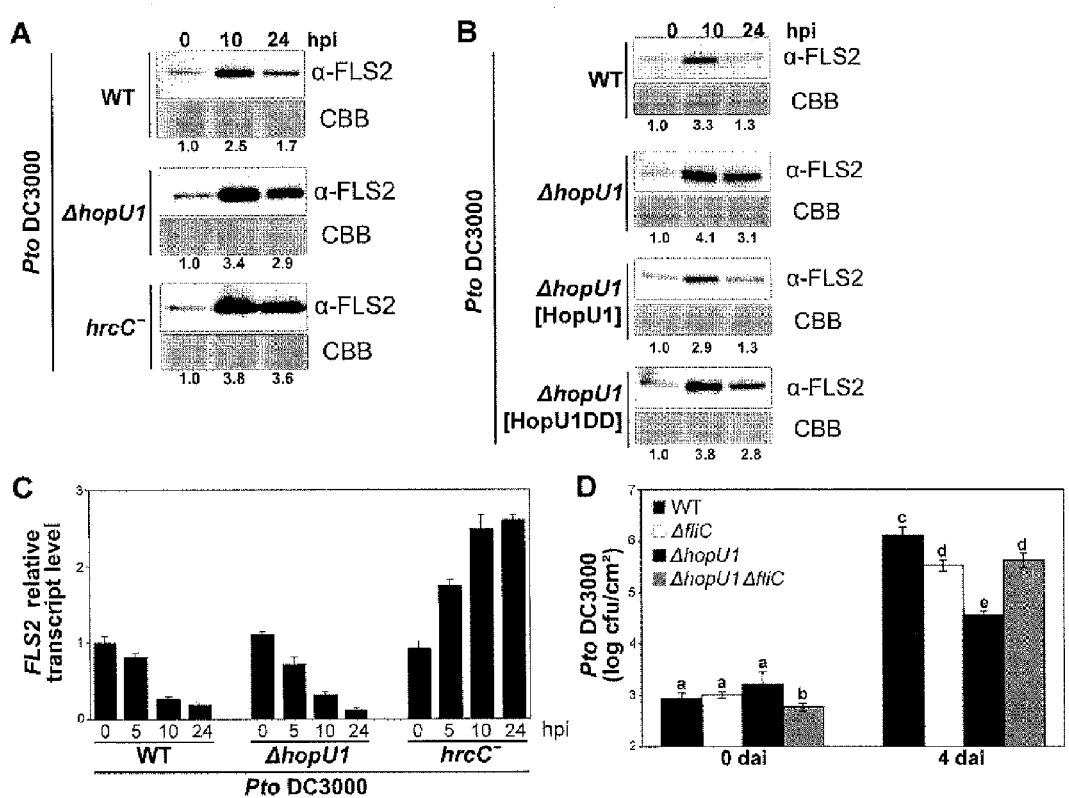
FIG. 7 shows that HopU1 inhibits FLS2 protein accumulation during infection. Panel (A) shows immunoblots with specific antibodies detecting endogenous FLS2 in Col-0 during bacterial infection after syringe-inoculation with Pto DC3000 (WT; inoculum: 5×10$^7$ cfu/mL), Pto DC3000 ΔhopU1 (inoculum: 10$^8$ cfu/mL), Pto DC3000 hrcC$^+$ (inoculum: 10$^8$ cfu/mL). hpi, hours post-infection; CBB, Coomassie Brilliant Blue. Values correspond to signal intensity of the FLS2-specific band from the immunoblots relative to the zero time-point. Panel (B) shows immunoblots with specific antibodies detecting endogenous FLS2 in Col-0 during bacterial infection after syringe-inoculation with Pto DC3000 (WT; inoculum: $5 \times 10^7$ cfu/mL), Pto DC3000 ΔhopU1 (inoculum: $10^8$ cfu/mL), Pto DC3000 ΔhopU1 [HopU1] (inoculum: $10^8$ cfu/mL), Pto DC3000 ΔhopU1 [HopU1DD] (inoculum: $10^8$ cfu/mL). hpi, hours post-infection; CBB, Coomassie Brilliant Blue. Values correspond to signal intensity of the FLS2-specific band from the immunoblots relative to the zero time-point. Panel (C) shows the FLS2 transcript level as measured by quantitative RT-PCR in Col-0 plants during bacterial infection after syringe-inoculation with Pto DC3000 (WT; inoculum: $5 \times 10^7$ cfu/mL), Pto DC3000 ΔhopU1 (inoculum: $10^8$ cfu/mL), Pto DC3000 hrcC$^+$ (inoculum: $10^8$ cfu/mL). hpi, hours post-infection. Panel (D) shows bacteria growth measured during pseudomonas infection in Col-0 plants, after syringe- (inoculum: $2 \times 10^5$ cfu/mL) or spray-inoculation (inoculum: $2 \times 10^8$ cfu/mL) with Pto DC3000 wild-type (WT) or the derivated strains ΔfliC, ΔhopU1 and ΔhopU1ΔfliC. Growth measured by colony forming units (cfu) two and/or four days after inoculation. Values are mean±SE (n=4). Statistical significance was assessed using the ANOVA test (P<0.001). dai, days after-inoculation. The results shown are representative of three independent experiments.

HopU1 Inhibits the Pathogen-Induced FLS2 Protein Accumulation During *Pseudomonas* Infection Because HopU1 inhibits GRP7-FLS2 mRNA binding (FIG. 6), it was asked whether HopU1's action could ultimately affect FLS2 protein levels after translocation into *A. thaliana* cells during Pto DC3000 infection, which would correspond to the most biologically-relevant observation. It was observed that the amount of FLS2 protein increases (3.6 to 3.8-fold) over 24 hours in leaves infected with Pto DC3000 hrcC$^+$ (unable to secrete any T3SEs and therefore unable to dampen PTI) (FIG. 7A), consistent with the previous observation that the expression of FLS2, EFR and other potential PRR-encoding genes is PAMP-inducible (see, for example, Zipfel et al., 2006, Cell, 125:749-760; and Zipfel et al., 2004, Nature, 428:764-767). Notably, this PAMP-induced accumulation is attenuated by T3SEs (FIG. 7A; compare hrcC$^+$ with WT). However, this T3SE-mediated suppression was much less marked after inoculation with Pto DC3000 ΔhopU1 (FIG. 7A; compare ΔhopU1 with WT). Importantly, expression of HopU1 in trans on a plasmid in Pto DC3000 ΔhopU1 restored the inhibition of FLS2 accumulation during infection, while trans-complementation with the catalytically inactive HopU1DD variant did not (FIG. 7B).

Notably, while the amount of cellular FLS2 mRNA increased during the first hours of infection with Pto DC3000 hrcC$^+$, it decreased to a similar level upon infection with Pto DC3000 WT and ΔhopU1 (FIG. 7C). The contrasting regulation and sensitivity to HopU1 of FLS2 mRNA and protein levels during infection further demonstrate that HopU1 regulates FLS2 post-transcriptionally, while other T3SEs already regulate FLS2 at the transcriptional level. Consistent with FLS2 being an important virulence target for HopU1, it was found that deletion of the flagellin-encoding gene FliC in the ΔhopU1 background (Pto DC3000 ΔhopU1 ΔfliC) suppress the virulence defect of Pto DC3000 ΔhopU1 and restore the virulence of Pto DC3000 ΔhopU1 ΔfliC to a comparable level as Pto DC3000 ΔfliC on WT *A. thaliana* plants (FIG. 7D). Together, these results indicate that HopU1 strongly affects the increased accumulation of FLS2 protein level normally observed during the first hours of *A. thaliana* infection by Pto DC3000.

Part B

Overexpression in Soybean

Example 1

Analysis of Soybean Genome

Sequence analysis of the soybean genome was performed to identify putative glycine-rich RNA binding proteins. The RNA-binding domain from the *A. thaliana* GRP7 protein was used as the query in the sequence analysis, and 12 soybean genes were identified. See the Table below and FIG. 16.

| Gene* | Gene Name* | SEQ ID NO (nucleic acid, amino acid) | % sequence identity to *A. thaliana* GRP7 (over the RNA-binding domain) |
|---|---|---|---|
| Glyma05g00400.1 | gmGRBP1d/GRBP1c/GRBP1e-1 | 15, 16 | 46 |
| Glyma05g00400.2 | gmGRBP1d/GRBP1c/GRBP1e-1 | 17, 18 | 46 |
| Glyma08g26900.1 | gmGRBP1d/GRBP1c/GRBP1e-2 | 19, 20 | 56 |
| Glyma11g36580.1 | gmGRBP1d/GRBP1c/GRBP1e-3 | 21, 22 | 46 |
| Glyma17g08630.1 | gmGRBP1d/GRBP1c/GRBP1e-4 | 23, 24 | 46 |
| Glyma18g00480.1 | gmGRBP1d/GRBP1c/GRBP1e-5 | 25, 26 | 46 |
| Glyma18g00480.2 | gmGRBP1d/GRBP1c/GRBP1e-5 | 27, 28 | 45 |
| Glyma18g50150.1 | gmGRBP1d/GRBP1c/GRBP1e-6 | 29, 30 | 58 |
| Glyma06g01470.1 | gmGRP7/gmGRBP3a-1 | 31, 32 | 75 |
| Glyma11g12480.1 | gmGRP7/gmGRBP3a-2 | 33, 34 | 81 |
| Glyma11g12490.1 | gmGRP7/gmGRBP3a-3 | 35, 36 | 80 |
| Glyma11g12510.2 | gmGRP7/gmGRBP3a-4 | 37, 38 | 74 |

*from PlantGDB website

The nucleic acid and amino acid sequence of AtGRP is shown in SEQ ID NOs: 39 & 40, respectively.

Two of the soybean sequences with the highest homology were analyzed in more detail. The putative RNA-binding portion of the sequence identified as Glyma06g01470 (SEQ ID NO:32) was determined to have 75% sequence identity to the RNA-binding portion of the *A. thaliana* GRP7 sequence. In addition, the putative RNA-binding portion of the sequence identified as Glyma11g12480 (SEQ ID NO:34) was determined to have 81% sequence identity to the RNA-binding portion of the *A. thaliana* GRP7 sequence. Significantly, both soybean sequences were determined to have Arginines at positions 47 and 49 (R47 and R49).

Example 2

Transformation of Soybean and Identification of Transgenic Plants

The coding sequences from the soybean genes were cloned into the binary vector, pPTN200, which is a member of the pPZP family of binary vectors (see, for example, Hajdukiewicz et al., 1994, Plant Mol. Biol., 25:989-94). The soybean sequences were placed under control of the 35S Cauliflower Mosaic Virus (CaMV) promoter with a duplicated enhancer (Benfey & Chua, 1990, Science, 250:959-66) and terminated by its 3' UTR.

The binary vector was introduced into soybean using *Agrobacterium*-mediated transformation. Specifically, the cotyledonary node system was used to generate transgenic soybean plants (see, for example, Hinchee et al., 1988, Bio/Technol., 6:915-22).

The pPTN200 vector carries a bar gene (Thompson et al., 1987, EMBO, 6:2519-23) under the control of the *Agrobacterium tumefaciens* nopaline synthase promoter (Pnos) and terminated using the 3' UTR of the nopaline synthase gene. Therefore, selection of transformants was performed using the herbicide, Basta.

Example 3

Evaluating the Plants' Response to Biotic Stress

Transgenic soybean plants overexpressing one or more of the soybean sequences are exposed to PAMP and their levels of callose and ROS are determined as an indicator of the immune response.

In addition, transgenic soybean plants overexpressing one or more of the soybean sequences are challenged with a number of pathogens to determine the plants' innate immunity response. For example, the transgenic soybean plants are exposed to bacterial pathogens such as, without limitation, *Pseudomonas syringae* pv. *glycinea* (bacterial blight);

viral pathogens including, for example, tobacco ringspot virus (bud blight) or soybean mosaic virus (soybean mosaic);

fungal pathogens such as *Septoria* glycines (brown spot), *Diaporthe phaseolorum* (pod and stem blight), *Peronospora manshurica* (downy mildew), *Phytophthora sojae* (*Phytophthora* rot), *Rhizoctonia solani* (*Rhizoctonia* stem rot), *Sclerotinia sclerotiorum* (*Sclerotinia* stem rot), *Phialophora gregata* (brown stem rot), *Fusarium solani* (sudden death syndrome), or *Macrophomina phaseolina* (charcoal root rot).

In addition to identifying visual indicators of pathogenicity (e.g., compared to a non-transgenic control plant), the presence and/or amount of one or more pathogens remaining on the plant is obtained (e.g., using bacterial or fungal spore counts or molecules techniques such as, for example, Southern blotting) compared to that remaining on a non-transgenic plant. It would be understood by those skilled in the art that the list of soybean pathogens provided herein is not exhaustive and is intended only to be exemplary. See, for example, Compendium of Soybean Diseases, 4$^{th}$ Ed., 1999, Hartman et al., eds., Amer. Phytopathol. Soc.

The transgenic soybean plants generally exhibit more resistance than non-transgenic soybean plants.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of increasing the innate immunity exhibited by a soybean plant comprising:
    introducing a transgene into a plurality of soybean cells to produce transgenic soybean cells, wherein the transgene comprises a nucleic acid sequence having at least 99% sequence identity to the nucleotide sequence of SEQ ID NO: 33 encoding soybean glycine rich RNA binding protein as set forth in SEQ ID NO: 34, wherein the nucleic acid sequence is operably linked to a promoter functional in soybean cells;
    regenerating transgenic soybean plants from the transgenic soybean cells;
    identifying at least one of said transgenic soybean plants expressing said transgene encoding said soybean glycine rich RNA binding protein;
    exposing at least one of said transgenic soybean plants expressing said transgene encoding said soybean glycine rich RNA binding protein to a biotic stress; and
    identifying at least one of said transgenic soybean plants that exhibits increased innate immunity in response to the biotic stress relative to a control plant.

2. The method of claim 1, wherein said transgene comprises the nucleic acid sequence of SEQ ID NO: 33.

3. The method of claim 1, wherein said biotic stress is selected from the group consisting of a pathogen-induced stress and a wound-induced stress.

4. The method of claim 1, wherein the promoter is a constitutive promoter.

5. A method of increasing the innate immunity exhibited by a soybean plant comprising:
    introducing a transgene into a plurality of soybean cells to produce transgenic soybean cells, wherein the transgene comprises a nucleic acid sequence that encodes a polypeptide having the amino acid sequence of SEQ ID NO: 34, wherein the nucleic acid sequence is operably linked to a promoter functional in soybean cells;
    regenerating transgenic soybean plants from the transgenic soybean cells;
    identifying at least one of said transgenic soybean plants expressing said transgene encoding said polypeptide;
    exposing at least one of said transgenic soybean plants expressing said transgene to a biotic stress; and
    identifying, at least one of said transgenic soybean plants that exhibits increased innate immunity in response to the biotic stress relative to a control plant.

6. The method of claim 5, wherein said biotic stress is selected from the group consisting of a pathogen-induced stress and a wound-induced stress.

7. The method of claim 5, wherein the promoter is a constitutive promoter.

* * * * *

UNITED STATES PATENT AND TRADEMARK OFFICE
CERTIFICATE OF CORRECTION

Page 1 of 1

PATENT NO. : 9,169,489 B2
APPLICATION NO. : 13/608702
DATED : October 27, 2015
INVENTOR(S) : James R. Alfano et al.

It is certified that error appears in the above-identified patent and that said Letters Patent is hereby corrected as shown below:

On the title page item 56

Column 2, Line 16 (Other Publications), delete "syringaetype" and insert -- syringae type --, therefor.

Column 2, Line 21 (Other Publications), delete "syringaetype" and insert -- syringae type --, therefor.

Column 2, Line 24 (Other Publications), delete "ArabidopsisReceptor" and insert -- Arabidopsis Receptor --, therefor.

Column 2, Line 28 (Other Publications), delete "syringaetype" and insert -- syringae type --, therefor.

Column 2, Line 33 (Other Publications), after "284-288", delete "Fu et al.".

Column 2, Line 34 (Other Publications), before ""Pseudomonas" insert -- Fu et al. --.

Column 2, Line 38 (Other Publications), delete "syringaepv." and insert -- syringae pv. --, therefor.

Column 2, Line 44 (Other Publications), delete "syringaeon" and insert -- syringae on --, therefor.

In the claims

Column 50, Line 32, In Claim 5, delete "identifying," and insert -- identifying --, therefor.

Signed and Sealed this
First Day of March, 2016

Michelle K. Lee
*Director of the United States Patent and Trademark Office*

UNITED STATES PATENT AND TRADEMARK OFFICE
CERTIFICATE OF CORRECTION

PATENT NO. : 9,169,489 B2
APPLICATION NO. : 13/608702
DATED : October 27, 2015
INVENTOR(S) : James R. Alfano et al.

It is certified that error appears in the above-identified patent and that said Letters Patent is hereby corrected as shown below:

In the Specification

In Column 1, please delete "The U.S. Government has certain rights in this invention pursuant to Grant No. R01 AI069146 awarded by the National Institute of Health" and insert --This invention was made with government support under R01 AI069146 awarded by the National Institutes of Health. The government has certain rights in the invention.--, therefor.

Signed and Sealed this
Fourteenth Day of March, 2023

Katherine Kelly Vidal
*Director of the United States Patent and Trademark Office*

SEQUENCE LISTING

```
<160> NUMBER OF SEQ ID NOS: 40

<210> SEQ ID NO 1
<211> LENGTH: 24
<212> TYPE: DNA
<213> ORGANISM: Artificial Sequence
<220> FEATURE:
<223> OTHER INFORMATION: oligonucleotide

<400> SEQUENCE: 1
tgcgctgcca gataatacac tatt                                          24

<210> SEQ ID NO 2
<211> LENGTH: 19
<212> TYPE: DNA
<213> ORGANISM: Artificial Sequence
<220> FEATURE:
<223> OTHER INFORMATION: oligonucleotide
```

-continued

<400> SEQUENCE: 2
tgctgcccaa catcaggtt                                             19

<210> SEQ ID NO 3
<211> LENGTH: 23
<212> TYPE: DNA
<213> ORGANISM: Artificial Sequence
<220> FEATURE:
<223> OTHER INFORMATION: oligonucleotide

<400> SEQUENCE: 3
actctcctcc aggggctaag gat                                        23

<210> SEQ ID NO 4
<211> LENGTH: 23
<212> TYPE: DNA
<213> ORGANISM: Artificial Sequence
<220> FEATURE:
<223> OTHER INFORMATION: oligonucleotide

<400> SEQUENCE: 4
agctaacagc tctccaggga tgg                                        23

<210> SEQ ID NO 5
<211> LENGTH: 20
<212> TYPE: DNA
<213> ORGANISM: Artificial Sequence
<220> FEATURE:
<223> OTHER INFORMATION: oligonucleotide

<400> SEQUENCE: 5
cggatgaagc agtacgagaa                                            20

<210> SEQ ID NO 6
<211> LENGTH: 21
<212> TYPE: DNA
<213> ORGANISM: Artificial Sequence
<220> FEATURE:
<223> OTHER INFORMATION: oligonucleotide

<400> SEQUENCE: 6
ccattcctga ggagaacttt g                                          21

<210> SEQ ID NO 7
<211> LENGTH: 24
<212> TYPE: DNA
<213> ORGANISM: Artificial Sequence
<220> FEATURE:
<223> OTHER INFORMATION: oligonucleotide

<400> SEQUENCE: 7
accgcctcct atctctccta cacc                                       24

<210> SEQ ID NO 8
<211> LENGTH: 23
<212> TYPE: DNA
<213> ORGANISM: Artificial Sequence
<220> FEATURE:
<223> OTHER INFORMATION: oligonucleotide

<400> SEQUENCE: 8
ctgggtcctc ttcagctggt aca                                        23

<210> SEQ ID NO 9
<211> LENGTH: 25

-continued

```
<212> TYPE: DNA
<213> ORGANISM: Artificial Sequence
<220> FEATURE:
<223> OTHER INFORMATION: oligonucleotide

<400> SEQUENCE: 9
tgatgacaga gctcttgaga ctgcc                                        25

<210> SEQ ID NO 10
<211> LENGTH: 31
<212> TYPE: DNA
<213> ORGANISM: Artificial Sequence
<220> FEATURE:
<223> OTHER INFORMATION: oligonucleotide

<400> SEQUENCE: 10
tcctcctcca ccctcgcgtc taccgccgcc a                                 31

<210> SEQ ID NO 11
<211> LENGTH: 25
<212> TYPE: DNA
<213> ORGANISM: Artificial Sequence
<220> FEATURE:
<223> OTHER INFORMATION: oligonucleotide

<400> SEQUENCE: 11
caatgatgaa gatcttcaaa ggacg                                        25

<210> SEQ ID NO 12
<211> LENGTH: 33
<212> TYPE: DNA
<213> ORGANISM: Artificial Sequence
<220> FEATURE:
<223> OTHER INFORMATION: oligonucleotide

<400> SEQUENCE: 12
ctcgtaacca ccaccgcctc ctcctgagta tcc                               33

<210> SEQ ID NO 13
<211> LENGTH: 27
<212> TYPE: DNA
<213> ORGANISM: Artificial Sequence
<220> FEATURE:
<223> OTHER INFORMATION: oligonucleotide

<400> SEQUENCE: 13
gatggtaccg aagtttagca gcaaagc                                      27

<210> SEQ ID NO 14
<211> LENGTH: 29
<212> TYPE: DNA
<213> ORGANISM: Artificial Sequence
<220> FEATURE:
<223> OTHER INFORMATION: oligonucleotide

<400> SEQUENCE: 14
gagctcgagg ttcatcaaaa ccaaatttc                                    29

<210> SEQ ID NO 15
<211> LENGTH: 825
<212> TYPE: DNA
<213> ORGANISM: Glycine max

<400> SEQUENCE: 15
atggctttct ttggtagaat tgggaattta ttaagacaga cagcaagcag gcaggttagt   60
```

```
tcagaattgc gatcatcccc ttcgtttttt caggctatac gcagtatgtc atctgctcca    120
agcacaaagc tgtttatcgg aggtgtttca tattctactg acgagcaaag tttgagggaa    180 gcttttcaa aatatggtga agttgttgat gctaggataa ttatggatcg tgaaactggt     240
agatccagag gatttggctt tattacatac acttcggttg aggaggcatc aagtgccatt    300
caggccttgg atggtcagga cctacatggt cgcccgatta gggtgaatta tgctaatgaa    360
agacctcgtg gatatggtgg cggtggcttt ggttcatacg gtgctgtagg tggcggtggc    420
tatgaaggtg gtagcagcta tcgtggtggt tatggtggtg acaactatag tcgaaatgat    480
gggagtggtt atggatatgg tggaggcagg tatggatcag gcggcaatta tggggacagt    540
ggctctggca ataactattc aggaggctat gctggtaatg ccggtggtgt aggcaatcat    600
gaaagctcta ctggttttgc cagtaatgga tatgatggaa gtgttgtgga tggtggtgtt    660
ggtgcaggta gtggcactag ctttgctgat ggctatgatg gaagtgcggg gtctgaattt    720
ggcagcagtg gccaattaga tagcaaagca agcagcaaag gagatgagga ttttggtgat    780
tacagggatg acaacgatgc agatgatttt gccaagaggg cttga                   825
```

<210> SEQ ID NO 16
<211> LENGTH: 274
<212> TYPE: PRT
<213> ORGANISM: Glycine max

<400> SEQUENCE: 16

```
Met Ala Phe Phe Gly Arg Ile Gly Asn Leu Leu Arg Gln Thr Ala Ser
 1               5                  10                  15

Arg Gln Val Ser Ser Glu Leu Arg Ser Ser Pro Ser Phe Phe Gln Ala
                20                  25                  30

Ile Arg Ser Met Ser Ser Ala Pro Ser Thr Lys Leu Phe Ile Gly Gly
            35                  40                  45

Val Ser Tyr Ser Thr Asp Glu Gln Ser Leu Arg Glu Ala Phe Ser Lys
        50                  55                  60

Tyr Gly Glu Val Val Asp Ala Arg Ile Ile Met Asp Arg Glu Thr Gly
 65                  70                  75                  80

Arg Ser Arg Gly Phe Gly Phe Ile Thr Tyr Thr Ser Val Glu Glu Ala
                 85                  90                  95

Ser Ser Ala Ile Gln Ala Leu Asp Gly Gln Asp Leu His Gly Arg Pro
            100                 105                 110

Ile Arg Val Asn Tyr Ala Asn Glu Arg Pro Arg Gly Tyr Gly Gly Gly
        115                 120                 125

Gly Phe Gly Ser Tyr Gly Ala Val Gly Gly Gly Tyr Glu Gly Gly
    130                 135                 140

Ser Ser Tyr Arg Gly Gly Tyr Gly Gly Asp Asn Tyr Ser Arg Asn Asp
145                 150                 155                 160

Gly Ser Gly Tyr Gly Tyr Gly Gly Gly Arg Tyr Gly Ser Gly Gly Asn
                165                 170                 175

Tyr Gly Asp Ser Gly Ser Gly Asn Asn Tyr Ser Gly Gly Tyr Ala Gly
            180                 185                 190

Asn Ala Gly Gly Val Gly Asn His Glu Ser Ser Thr Gly Phe Ala Ser
        195                 200                 205

Asn Gly Tyr Asp Gly Ser Val Val Asp Gly Gly Val Gly Ala Gly Ser
    210                 215                 220

Gly Thr Ser Phe Ala Asp Gly Tyr Asp Gly Ser Ala Gly Ser Glu Phe
225                 230                 235                 240
```

Gly Ser Ser Gly Gln Leu Asp Ser Lys Ala Ser Lys Gly Asp Glu
                245                 250                 255

Asp Phe Gly Asp Tyr Arg Asp Asp Asn Asp Ala Asp Phe Ala Lys
            260                 265                 270

Arg Ala

<210> SEQ ID NO 17
<211> LENGTH: 738
<212> TYPE: DNA
<213> ORGANISM: Glycine max

<400> SEQUENCE: 17

```
atggctttct ttggtagaat tgggaattta ttaagacaga cagcaagcag gcaggttagt      60
tcagaattgc gatcatcccc ttcgtttttt caggctatac gcagtatgtc atctgctcca     120
agcacaaagc tgtttatcgg aggtgtttca tattctactg acgagcaaag tttgagggaa     180
gcttttcaa atatggtga agttgttgat gctaggataa ttatggatcg tgaaactggt      240
agatccagag gatttggctt tattacatac acttcggttg aggaggcatc aagtgccatt     300
caggccttgg atggtcagga cctacatggt cgcccgatta gggtgaatta tgctaatgaa     360
agacctcgtg gatatggtgg cggtggcttt ggttcatacg gtgctgtagg tggcggtggc     420
tatgaaggtg gtagcagcta tcgtggtggt tatggtggtg acaactatag tcgaaatgat     480
gggagtggtt atggatatgg tggaggcaat catgaaagct ctactggttt tgccagtaat     540
ggatatgatg gaagtgttgt ggatggtggt gttggtgcag gtagtggcac tagctttgct     600
gatggctatg atggaagtgc ggggtctgaa tttggcagca gtggccaatt agatagcaaa     660
gcaagcagca aaggagatga ggattttggt gattacaggg atgacaacga tgcagatgat     720
tttgccaaga gggcttga                                                  738
```

<210> SEQ ID NO 18
<211> LENGTH: 245
<212> TYPE: PRT
<213> ORGANISM: Glycine max

<400> SEQUENCE: 18

Met Ala Phe Phe Gly Arg Ile Gly Asn Leu Leu Arg Gln Thr Ala Ser
 1               5                  10                  15

Arg Gln Val Ser Glu Leu Arg Ser Ser Pro Ser Phe Phe Gln Ala
            20                  25                  30

Ile Arg Ser Met Ser Ser Ala Pro Ser Thr Lys Leu Phe Ile Gly Gly
        35                  40                  45

Val Ser Tyr Ser Thr Asp Glu Gln Ser Leu Arg Glu Ala Phe Ser Lys
    50                  55                  60

Tyr Gly Glu Val Val Asp Ala Arg Ile Ile Met Asp Arg Glu Thr Gly
65                  70                  75                  80

Arg Ser Arg Gly Phe Gly Phe Ile Thr Tyr Thr Ser Val Glu Glu Ala
                85                  90                  95

Ser Ser Ala Ile Gln Ala Leu Asp Gly Gln Asp Leu His Gly Arg Pro
            100                 105                 110

Ile Arg Val Asn Tyr Ala Asn Glu Arg Pro Arg Gly Tyr Gly Gly Gly
        115                 120                 125

Gly Phe Gly Ser Tyr Gly Ala Val Gly Gly Gly Tyr Glu Gly Gly
    130                 135                 140

Ser Ser Tyr Arg Gly Gly Tyr Gly Gly Asp Asn Tyr Ser Arg Asn Asp
145                 150                 155                 160

```
Gly Ser Gly Tyr Gly Tyr Gly Gly Asn His Glu Ser Thr Gly
            165                 170                 175

Phe Ala Ser Asn Gly Tyr Asp Gly Ser Val Val Asp Gly Val Gly
            180                 185                 190

Ala Gly Ser Gly Thr Ser Phe Ala Asp Gly Tyr Asp Gly Ser Ala Gly
        195                 200                 205

Ser Glu Phe Gly Ser Ser Gly Gln Leu Asp Ser Lys Ala Ser Ser Lys
    210                 215                 220

Gly Asp Glu Asp Phe Gly Asp Tyr Arg Asp Asn Asp Ala Asp Asp
225             230                 235                 240

Phe Ala Lys Arg Ala
            245
```

<210> SEQ ID NO 19
<211> LENGTH: 738
<212> TYPE: DNA
<213> ORGANISM: Glycine max

<400> SEQUENCE: 19

| | | |
|---|---|---|
| atggcgttct taaataaaat tggaaatctg gtcaagaatt ctgctgtcaa gcacatcaat | 60 |
| caagattttt cagtgtctac cccatcactt ttccaagcaa ttagatccat gtcatctgca | 120 |
| aagcttttg tcggaggtat ttcttacagc actgatgata tgagtttgcg agagtctttt | 180 |
| gctcgctatg gagaagtaat agatgtcaag gtcattatgg atcgtgaaac tggcaggtca | 240 |
| agaggttttg gcttcataac ttttgcaaca agtgaggatg catcttctgc cattcagggc | 300 |
| atggatggtc aggatcttca tggtcgcagg atacgggtga attatgctac agaaaggtca | 360 |
| cgtccagggt ttggtggtga tggtggatat aggggcagtg gtggcagcga tggctacaat | 420 |
| agggtggaa actatggagg tggatataac agtggcagcg atggctacaa taggggtgga | 480 |
| aactatggaa gtggcaatta taatgttaca agcagctata gtgatggcaa tgctgaaact | 540 |
| agttacacta gtggtgctaa tgctggtaat taccaattca tgaaaattc tggtggagtt | 600 |
| tttggctcag ctagcggtga attcagcagc aaccaaaatg acgcaacagg tgcagacaat | 660 |
| gatgaattca ttgagccact tgaagacaat gtgagggaga caatgatga acctactgac | 720 |
| tacgctcaga accgctga | 738 |

<210> SEQ ID NO 20
<211> LENGTH: 245
<212> TYPE: PRT
<213> ORGANISM: Glycine max

<400> SEQUENCE: 20

```
Met Ala Phe Leu Asn Lys Ile Gly Asn Leu Val Lys Asn Ser Ala Val
1               5                   10                  15

Lys His Ile Asn Gln Asp Phe Ser Val Ser Thr Pro Ser Leu Phe Gln
            20                  25                  30

Ala Ile Arg Ser Met Ser Ser Ala Lys Leu Phe Val Gly Gly Ile Ser
        35                  40                  45

Tyr Ser Thr Asp Asp Met Ser Leu Arg Glu Ser Phe Ala Arg Tyr Gly
    50                  55                  60

Glu Val Ile Asp Val Lys Val Ile Met Asp Arg Glu Thr Gly Arg Ser
65              70                  75                  80

Arg Gly Phe Gly Phe Ile Thr Phe Ala Thr Ser Glu Asp Ala Ser Ser
            85                  90                  95
```

Ala Ile Gln Gly Met Asp Gly Gln Asp Leu His Gly Arg Arg Ile Arg
                100                 105                 110

Val Asn Tyr Ala Thr Glu Arg Ser Arg Pro Gly Phe Gly Gly Asp Gly
            115                 120                 125

Gly Tyr Arg Gly Ser Gly Ser Asp Gly Tyr Asn Arg Gly Gly Asn
        130                 135                 140

Tyr Gly Gly Tyr Asn Ser Gly Ser Asp Gly Tyr Asn Arg Gly Gly
145                 150                 155                 160

Asn Tyr Gly Ser Gly Asn Tyr Asn Val Thr Ser Ser Tyr Ser Asp Gly
                165                 170                 175

Asn Ala Glu Thr Ser Tyr Thr Ser Gly Ala Asn Ala Gly Asn Tyr Gln
            180                 185                 190

Phe Asn Glu Asn Ser Gly Gly Val Phe Gly Ser Ala Ser Gly Glu Phe
        195                 200                 205

Ser Ser Asn Gln Asn Asp Ala Thr Gly Ala Asp Asn Asp Glu Phe Ile
        210                 215                 220

Glu Pro Leu Glu Asp Asn Val Arg Glu Asn Asn Asp Glu Pro Thr Asp
225                 230                 235                 240

Tyr Ala Gln Asn Arg
            245

<210> SEQ ID NO 21
<211> LENGTH: 438
<212> TYPE: DNA
<213> ORGANISM: Glycine max

<400> SEQUENCE: 21
atggccttct gtaataaggt tggaaatgtc ttgaggcagg gtgctgctcg cagcacacaa     60
gcacctgttt catccatgct taattacatt cgctgcatgt cttcaagcaa gcttttatt    120 ggaggccttt catatggagt tgacgatcag tctcttaagg atgcattttc tggctttgga    180
gatgtggttg atgcaaaagt tataactgac agagactctg gaagatcaag gggatttgga    240
tttgtcaact tctccaatga tgagtctgca agttcggcac tctctgcaat ggatgggaag    300
atgggcgaag cattagggta tcctatgcaa atgatagacc ttctggacct caatctggcg    360
gcggcggcgg tggtggttat cgcagtgggg gttttggcgg cgggtggtga ttttgcttct    420
cgcaatggtg gttggtga                                                  438

<210> SEQ ID NO 22
<211> LENGTH: 145
<212> TYPE: PRT
<213> ORGANISM: Glycine max

<400> SEQUENCE: 22

Met Ala Phe Cys Asn Lys Val Gly Asn Val Leu Arg Gln Gly Ala Ala
 1               5                  10                  15

Arg Ser Thr Gln Ala Pro Val Ser Ser Met Leu Asn Tyr Ile Arg Cys
            20                  25                  30

Met Ser Ser Ser Lys Leu Phe Ile Gly Gly Leu Ser Tyr Gly Val Asp
        35                  40                  45

Asp Gln Ser Leu Lys Asp Ala Phe Ser Gly Phe Gly Asp Val Val Asp
    50                  55                  60

Ala Lys Val Ile Thr Asp Arg Asp Ser Gly Arg Ser Arg Gly Phe Gly
65                  70                  75                  80

Phe Val Asn Phe Ser Asn Asp Glu Ser Ala Ser Ser Ala Leu Ser Ala
                85                  90                  95

Met Asp Gly Lys Met Gly Glu Ala Leu Gly Tyr Pro Met Gln Met Ile
              100                 105                 110

Asp Leu Leu Asp Leu Asn Leu Ala Ala Ala Val Val Ile Ala
            115                 120                 125

Val Gly Val Leu Ala Ala Gly Gly Asp Phe Ala Ser Arg Asn Gly Gly
130                 135                 140

Trp
145

<210> SEQ ID NO 23
<211> LENGTH: 828
<212> TYPE: DNA
<213> ORGANISM: Glycine max

<400> SEQUENCE: 23

| | |
|---|---|
| atggctttct ttggtagaat tgggaatttg ttacgacaga cagcgagcag gcaggttagt | 60 |
| tcaaaattgc gttcgccccc ttcatttttt caggctatac gctgtatgtc atctgcccca | 120 |
| agcacaaaac tgtttattgg aggtgtttca tattctactg acgagcaaag cttgagggaa | 180 |
| gcttttcaa aatatggtga agttgttgat gctcggataa ttatggatcg tgaaactggt | 240 |
| agatccagag gatttggctt attacatac acttcggttg aggaggcatc aagtgccatt | 300 |
| caggccttgg atggtcagga tcttcatggt cgcccaatta gggtgaatta tgctaatgaa | 360 |
| agacctcgtg gatatggtgg tggtggcggc ggctttggtt catatggtgc tgtaggtggc | 420 |
| ggtggttatg aaggtggtgg tggcagcggt tatcgtggaa atgtttctga tggttatggt | 480 |
| ggtggcaact atagtcgaaa tgatgggggt ggttatggat atggtgcagg cagttatgga | 540 |
| tcaggcggca attatgggga cagtggccct ggcaataact actcgggagg ctatagtggt | 600 |
| agtaacagtg gacattttgg tgatgccggt agtgtaggca atcatgaaag ctctactggt | 660 |
| tttgccggta atggatatga tggaagtgtc gtggatggcg tgttggtgc agggtcggaa | 720 |
| tttggcagca gtggccaatt agatagcaaa acaagcagca atggagatga gggtttggg | 780 |
| gattacaggg atgacaacga tgcagataat tttgccaaga gggcttga | 828 |

<210> SEQ ID NO 24
<211> LENGTH: 275
<212> TYPE: PRT
<213> ORGANISM: Glycine max

<400> SEQUENCE: 24

Met Ala Phe Phe Gly Arg Ile Gly Asn Leu Leu Arg Gln Thr Ala Ser
 1               5                  10                  15

Arg Gln Val Ser Ser Lys Leu Arg Ser Pro Ser Phe Phe Gln Ala
            20                  25                  30

Ile Arg Cys Met Ser Ser Ala Pro Ser Thr Lys Leu Phe Ile Gly Gly
         35                  40                  45

Val Ser Tyr Ser Thr Asp Glu Gln Ser Leu Arg Glu Ala Phe Ser Lys
     50                  55                  60

Tyr Gly Glu Val Val Asp Ala Arg Ile Ile Met Asp Arg Glu Thr Gly
65                  70                  75                  80

Arg Ser Arg Gly Phe Gly Phe Ile Thr Tyr Thr Ser Val Glu Glu Ala
                 85                  90                  95

Ser Ser Ala Ile Gln Ala Leu Asp Gly Gln Asp Leu His Gly Arg Pro
             100                 105                 110

Ile Arg Val Asn Tyr Ala Asn Glu Arg Pro Arg Gly Tyr Gly Gly Gly

```
                 115                 120                 125
Gly Gly Gly Phe Gly Ser Tyr Gly Ala Val Gly Gly Gly Tyr Glu
            130                 135                 140
Gly Gly Gly Gly Ser Gly Tyr Arg Gly Asn Val Ser Asp Gly Tyr Gly
145                 150                 155                 160
Gly Gly Asn Tyr Ser Arg Asn Asp Gly Gly Tyr Gly Tyr Gly Ala
                165                 170                 175
Gly Ser Tyr Gly Ser Gly Gly Asn Tyr Gly Asp Ser Gly Pro Gly Asn
            180                 185                 190
Asn Tyr Ser Gly Gly Tyr Ser Gly Ser Asn Ser Gly His Phe Gly Asp
        195                 200                 205
Ala Gly Ser Val Gly Asn His Glu Ser Ser Thr Gly Phe Ala Gly Asn
        210                 215                 220
Gly Tyr Asp Gly Ser Val Val Asp Gly Gly Val Gly Ala Gly Ser Glu
225                 230                 235                 240
Phe Gly Ser Ser Gly Gln Leu Asp Ser Lys Thr Ser Ser Asn Gly Asp
            245                 250                 255
Glu Gly Phe Gly Asp Tyr Arg Asp Asp Asn Asp Ala Asp Asn Phe Ala
            260                 265                 270
Lys Arg Ala
        275

<210> SEQ ID NO 25
<211> LENGTH: 432
<212> TYPE: DNA
<213> ORGANISM: Glycine max

<400> SEQUENCE: 25
atggcgttct gtaataaggt tggaaatgtc ttgaggcagg gtgctgctcg cagcacacat      60
gcccctgttg cgtccatgct taattacatc cgctgcatgt cttcaagcaa gcttttcatt     120
ggaggccttt catatggagt tgatgaccag tctcttaagg atgcattttc tggctttgga     180
gatgtggttg atgcaaaagt tataactgat agagacagtg aagatcaag ggatttgga     240 tttgtcaact ctccaatga tgagtctgca agttcggcac tctctgcaat ggacgggaag     300
gatctaaatg ggcgaagcat tcgggtatcc tatgcaaatg ataaaccatc tgcacctcga     360
cctggtggcg gtggcggtta tcgtggcggg gattatgatg gtgattttgc ttctcgtagt     420
ggtggttggt ga                                                         432

<210> SEQ ID NO 26
<211> LENGTH: 143
<212> TYPE: PRT
<213> ORGANISM: Glycine max

<400> SEQUENCE: 26

Met Ala Phe Cys Asn Lys Val Gly Asn Val Leu Arg Gln Gly Ala Ala
1               5                   10                  15
Arg Ser Thr His Ala Pro Val Ala Ser Met Leu Asn Tyr Ile Arg Cys
            20                  25                  30
Met Ser Ser Ser Lys Leu Phe Ile Gly Gly Leu Ser Tyr Gly Val Asp
        35                  40                  45
Asp Gln Ser Leu Lys Asp Ala Phe Ser Gly Phe Gly Asp Val Val Asp
    50                  55                  60
Ala Lys Val Ile Thr Asp Arg Asp Ser Gly Arg Ser Arg Gly Phe Gly
65                  70                  75                  80
```

```
Phe Val Asn Phe Ser Asn Asp Glu Ser Ala Ser Ser Ala Leu Ser Ala
                 85                  90                  95

Met Asp Gly Lys Asp Leu Asn Gly Arg Ser Ile Arg Val Ser Tyr Ala
            100                 105                 110

Asn Asp Lys Pro Ser Ala Pro Arg Pro Gly Gly Gly Gly Tyr Arg
            115                 120                 125

Gly Gly Asp Tyr Asp Gly Asp Phe Ala Ser Arg Ser Gly Gly Trp
        130                 135                 140
```

<210> SEQ ID NO 27
<211> LENGTH: 426
<212> TYPE: DNA
<213> ORGANISM: Glycine max

<400> SEQUENCE: 27

```
atggcgttct gtaataaggt tggaaatgtc ttgaggcagg gtgctgctcg cagcacacat      60
gcccctgttg cgtccatgct taattacatc cgctgcatgt cttcaagcaa gcttttcatt    120
ggaggccttt catatggagt tgatgaccag tctcttaagg atgcattttc tggctttgga    180
gatgtggttg atgttataac tgatagagac agtggaagat caaggggatt tggatttgtc    240
aacttctccc atgatgagtc tgcaagttcg gcactctctg caatggacgg aaggatctca    300
aatgggcgaa gcattcgggt atcctatgca aatgataaac catctgcacc tcgacctggt    360
ggcggtggcg gttatcgtgg cggggattat gatggtgatt ttgcttctcg tagtggtggt    420
tggtga                                                              426
```

<210> SEQ ID NO 28
<211> LENGTH: 141
<212> TYPE: PRT
<213> ORGANISM: Glycine max

<400> SEQUENCE: 28

```
Met Ala Phe Cys Asn Lys Val Gly Asn Val Leu Arg Gln Gly Ala Ala
 1               5                  10                  15

Arg Ser Thr His Ala Pro Val Ala Ser Met Leu Asn Tyr Ile Arg Cys
             20                  25                  30

Met Ser Ser Ser Lys Leu Phe Ile Gly Gly Leu Ser Tyr Gly Val Asp
         35                  40                  45

Asp Gln Ser Leu Lys Asp Ala Phe Ser Gly Phe Gly Asp Val Val Asp
     50                  55                  60

Val Ile Thr Asp Arg Asp Ser Gly Arg Ser Arg Gly Phe Gly Phe Val
 65                  70                  75                  80

Asn Phe Ser Asn Asp Glu Ser Ala Ser Ser Ala Leu Ser Ala Met Asp
                 85                  90                  95

Gly Lys Asp Leu Asn Gly Arg Ser Ile Arg Val Ser Tyr Ala Asn Asp
            100                 105                 110

Lys Pro Ser Ala Pro Arg Pro Gly Gly Gly Gly Tyr Arg Gly Gly
            115                 120                 125

Asp Tyr Asp Gly Asp Phe Ala Ser Arg Ser Gly Gly Trp
        130                 135                 140
```

<210> SEQ ID NO 29
<211> LENGTH: 735
<212> TYPE: DNA
<213> ORGANISM: Glycine max

<400> SEQUENCE: 29

```
atggcgttct taaataaaat tggaaatctg ctcaagaatt ctgctgtcaa gcacatcaat      60
caggattttt cggcgtctac cccttcactt ttccaagcaa ttagatccat gtcatctgca     120
aagcttttcg tcggaggtat ttcttacagc actgatgata tgagtttgcg agagtctttt     180
gctcgctatg gagaagtaat tgatggcaag gttattatgg atcgtgaaac tggcaggtca     240
agaggttttg gctttgtaac ttttgcaaca agtgaggatg catcttctgc cattcagggc     300
atggatggcc aggatcttca tggtcggagg atacgggtga attatgctac agaaaggtca     360
cgtccagggt ttggtggtga tggtggatat ggcagtggtg gtggtggcta caatgggggt     420
ggaaactatg gaagtggagg tggatatggt ggtggtggtg gctataatag ggtggaaac      480
tatggaagtg gcggttataa tgttactagc agctatagtg gtggcaatgc tgaaactagt     540
tacactggtg gtggtaatgc tagtaattac caattcaatg aaaactctgg tggagatttt     600
ggctcagcta gcggtgaatt cagcagcaac caaaatgaca cagcaggtgc agacaatgat     660
gaattcattg agccacttga agacaatgtg agggagaaca atgatggacc taccgactac     720
gctcagaacc gctga                                                     735

<210> SEQ ID NO 30
<211> LENGTH: 244
<212> TYPE: PRT
<213> ORGANISM: Glycine max

<400> SEQUENCE: 30

Met Ala Phe Leu Asn Lys Ile Gly Asn Leu Leu Lys Asn Ser Ala Val
1               5                   10                  15

Lys His Ile Asn Gln Asp Phe Ser Ala Ser Thr Pro Ser Leu Phe Gln
            20                  25                  30

Ala Ile Arg Ser Met Ser Ser Ala Lys Leu Phe Val Gly Gly Ile Ser
        35                  40                  45

Tyr Ser Thr Asp Asp Met Ser Leu Arg Glu Ser Phe Ala Arg Tyr Gly
    50                  55                  60

Glu Val Ile Asp Gly Lys Val Ile Met Asp Arg Glu Thr Gly Arg Ser
65                  70                  75                  80

Arg Gly Phe Gly Phe Val Thr Phe Ala Thr Ser Glu Asp Ala Ser Ser
                85                  90                  95

Ala Ile Gln Gly Met Asp Gly Gln Asp Leu His Gly Arg Arg Ile Arg
            100                 105                 110

Val Asn Tyr Ala Thr Glu Arg Ser Arg Pro Gly Phe Gly Gly Asp Gly
        115                 120                 125

Gly Tyr Gly Ser Gly Gly Gly Gly Tyr Asn Gly Gly Gly Asn Tyr Gly
    130                 135                 140

Ser Gly Gly Gly Tyr Gly Gly Gly Gly Tyr Asn Arg Gly Gly Asn
145                 150                 155                 160

Tyr Gly Ser Gly Gly Tyr Asn Val Thr Ser Ser Tyr Ser Gly Gly Asn
                165                 170                 175

Ala Glu Thr Ser Tyr Thr Gly Gly Gly Asn Ala Ser Asn Tyr Gln Phe
            180                 185                 190

Asn Glu Asn Ser Gly Gly Asp Phe Gly Ser Ala Ser Gly Glu Phe Ser
        195                 200                 205

Ser Asn Gln Asn Asp Thr Ala Gly Ala Asp Asn Asp Glu Phe Ile Glu
    210                 215                 220

Pro Leu Glu Asp Asn Val Arg Glu Asn Asn Asp Gly Pro Thr Asp Tyr
225                 230                 235                 240
```

Ala Gln Asn Arg

<210> SEQ ID NO 31
<211> LENGTH: 549
<212> TYPE: DNA
<213> ORGANISM: Glycine max

<400> SEQUENCE: 31

```
atggcttctg cagaagtaga gttccgatgc tttgttggtg ggcttgcttg ggccaccgac    60
cacgatgctc tcgagaaagc cttctctcaa tttggcgaaa tcgtcgaatc gaaggtcatc   120
aacgatcgtg aaactggaag atccagaggg tttggatttg tgaccttcgc cacagagcag   180
gcgatgagag acgcaattga aggaatgaac ggccagaacc tcgacggtcg taatataacc   240
gtgaacgagg ctcaatcccg tggaaaaggt ggcggcggcg gcggcggcgg ctacggagga   300
ggtggtggtg gttacggtgg cggcggaggt tacagccgcg gtgaggagga atatggtggc   360
ggaggaggcc gccgtgaagg tggttataac cgcaacggtg gtggaggagg atatggtggc   420
ggtggcggcg gatatggagg tggtggaggt tatggtggcg gtgggagaga ccgtggatat   480
ggtggtgatg gtgggtcccg ctactcgaga ggaggcggtg gttcggatgg aggaagctgg   540
aggaattaa                                                           549
```

<210> SEQ ID NO 32
<211> LENGTH: 182
<212> TYPE: PRT
<213> ORGANISM: Glycine max

<400> SEQUENCE: 32

Met Ala Ser Ala Glu Val Glu Phe Arg Cys Phe Val Gly Gly Leu Ala
1               5                   10                  15

Trp Ala Thr Asp His Asp Ala Leu Glu Lys Ala Phe Ser Gln Phe Gly
            20                  25                  30

Glu Ile Val Glu Ser Lys Val Ile Asn Asp Arg Glu Thr Gly Arg Ser
        35                  40                  45

Arg Gly Phe Gly Phe Val Thr Phe Ala Thr Glu Gln Ala Met Arg Asp
    50                  55                  60

Ala Ile Glu Gly Met Asn Gly Gln Asn Leu Asp Gly Arg Asn Ile Thr
65                  70                  75                  80

Val Asn Glu Ala Gln Ser Arg Gly Lys Gly Gly Gly Gly Gly Gly Gly
                85                  90                  95

Gly Tyr Gly Gly Gly Gly Gly Gly Tyr Gly Gly Gly Gly Gly Tyr Ser
            100                 105                 110

Arg Gly Gly Gly Gly Tyr Gly Gly Gly Gly Arg Arg Glu Gly Gly
        115                 120                 125

Tyr Asn Arg Asn Gly Gly Gly Gly Tyr Gly Gly Gly Gly Gly Gly
    130                 135                 140

Tyr Gly Gly Gly Gly Tyr Gly Gly Gly Gly Arg Asp Arg Gly Tyr
145                 150                 155                 160

Gly Gly Asp Gly Gly Ser Arg Tyr Ser Arg Gly Gly Gly Gly Ser Asp
                165                 170                 175

Gly Gly Ser Trp Arg Asn
            180

<210> SEQ ID NO 33
<211> LENGTH: 471
<212> TYPE: DNA
<213> ORGANISM: Glycine max

```
<400> SEQUENCE: 33
atggcttctg cggatgttga ataccgatgc tttgttggtg ggctcgcttg ggccactgac      60
aactacgatc tggagaaagc cttctctcag tacggtgacg tcgttgaatc gaagattatc    120
aacgatcgtg agactggaag atccagggga tttggatttg ttaccttcgc ctccgaggat    180
tcaatgaggg atgcgatcga agggatgaac ggtcagaacc ttgatggacg caacatcact    240
gtgaacgaag ctcagtcccg cggaagccgc ggtggaggcg gtggcggtta cggaagtggc    300
ggtggataca accgcagtgg tggtgctgga ggatacggtg ccgtcgggaa aggtgcatat    360
aaccgtaacg gtggtggtta tggcggtgac agagaccatc gttacggacc ttacggggac    420
ggtggatcac gctactctcg tggtggtggt gatggaagct ggagaaatta g             471

<210> SEQ ID NO 34
<211> LENGTH: 156
<212> TYPE: PRT
<213> ORGANISM: Glycine max

<400> SEQUENCE: 34
```

Met Ala Ser Ala Asp Val Glu Tyr Arg Cys Phe Val Gly Gly Leu Ala
1               5                   10                  15

Trp Ala Thr Asp Asn Tyr Asp Leu Glu Lys Ala Phe Ser Gln Tyr Gly
            20                  25                  30

Asp Val Val Glu Ser Lys Ile Ile Asn Asp Arg Glu Thr Gly Arg Ser
        35                  40                  45

Arg Gly Phe Gly Phe Val Thr Phe Ala Ser Glu Asp Ser Met Arg Asp
    50                  55                  60

Ala Ile Glu Gly Met Asn Gly Gln Asn Leu Asp Gly Arg Asn Ile Thr
65                  70                  75                  80

Val Asn Glu Ala Gln Ser Arg Gly Ser Arg Gly Gly Gly Gly Gly Gly
                85                  90                  95

Tyr Gly Ser Gly Gly Gly Tyr Asn Arg Ser Gly Gly Ala Gly Gly Tyr
            100                 105                 110

Gly Gly Arg Arg Glu Gly Ala Tyr Asn Arg Asn Gly Gly Gly Tyr Gly
        115                 120                 125

Gly Asp Arg Asp His Arg Tyr Gly Pro Tyr Gly Asp Gly Gly Ser Arg
    130                 135                 140

Tyr Ser Arg Gly Gly Gly Asp Gly Ser Trp Arg Asn
145                 150                 155

```
<210> SEQ ID NO 35
<211> LENGTH: 432
<212> TYPE: DNA
<213> ORGANISM: Glycine max

<400> SEQUENCE: 35
atgttatcca tggcttctgc atatgttgag taccgttgct tgttggtgg gctcgcttgg      60 gccacagacg atcatgcctt ggagaaagcc ttctctcact acggcaacat cgttgaatcg    120
aagattatca cgatcgtga gaccggaagg tccaggggat ttggatttgt taccttcgcc    180
tcggagaatt caatgaagga tgcgatcgaa gggatgaacg tcagaacct tgacggacgt    240 aacataactg tgaacgaagc tcagtcccgc ggcagccgcg gtggatacgg tggtcgtcgt    300
gaaggtggat ataaccgtgg tggtggaggc tatgagggg gtggttatgg tggtgacaga    360
gattgtggtt acggtgacgg tggttcacgc tactctcgtg gtggcgatgt caatggaagc    420
```
cggagaaact ag                                                              432

<210> SEQ ID NO 36
<211> LENGTH: 143
<212> TYPE: PRT
<213> ORGANISM: Glycine max

<400> SEQUENCE: 36

Met Leu Ser Met Ala Ser Ala Tyr Val Glu Tyr Arg Cys Phe Val Gly
1               5                   10                  15

Gly Leu Ala Trp Ala Thr Asp Asp His Ala Leu Glu Lys Ala Phe Ser
            20                  25                  30

His Tyr Gly Asn Ile Val Glu Ser Lys Ile Ile Asn Asp Arg Glu Thr
        35                  40                  45

Gly Arg Ser Arg Gly Phe Gly Phe Val Thr Phe Ala Ser Glu Asn Ser
    50                  55                  60

Met Lys Asp Ala Ile Glu Gly Met Asn Gly Gln Asn Leu Asp Gly Arg
65                  70                  75                  80

Asn Ile Thr Val Asn Glu Ala Gln Ser Arg Gly Ser Arg Gly Gly Tyr
                85                  90                  95

Gly Gly Arg Arg Glu Gly Gly Tyr Asn Arg Gly Gly Gly Tyr Gly
            100                 105                 110

Gly Gly Gly Tyr Gly Gly Asp Arg Asp Cys Gly Tyr Gly Asp Gly Gly
        115                 120                 125

Ser Arg Tyr Ser Arg Gly Gly Asp Val Asn Gly Ser Arg Arg Asn
    130                 135                 140

<210> SEQ ID NO 37
<211> LENGTH: 408
<212> TYPE: DNA
<213> ORGANISM: Glycine max

<400> SEQUENCE: 37
atggcttctg cagatgttga gttccgttgc tttgttggtg ggcttgcttg ggtcaccggc         60
aacgatgccc tcgagaaagc cttttcaatc tacggcgaca tcgttgaatc gaaggttatc        120
aacgaccgtg agactggaag gtccagagga ttcggatttg tgaccttcgc ctcagagcag        180
tcaatgaaag atgcgatcgc aggaatgaac ggccaggacc ttgacggccg taacatcact        240
gtcaacgaag ctcagacccg cgccagccgt ggtggtggtg gaggcggtgg tttcggaagt        300
ggtggaggat acggcggtgg tagagaccgt ggttacggtg gtgatggtgg ttctcgctac        360
tctcgcggtg gggaaggcgg tggatccgat ggaaactgga gaaattag                     408

<210> SEQ ID NO 38
<211> LENGTH: 135
<212> TYPE: PRT
<213> ORGANISM: Glycine max

<400> SEQUENCE: 38

Met Ala Ser Ala Asp Val Glu Phe Arg Cys Phe Val Gly Gly Leu Ala
1               5                   10                  15

Trp Val Thr Gly Asn Asp Ala Leu Glu Lys Ala Phe Ser Ile Tyr Gly
            20                  25                  30

Asp Ile Val Glu Ser Lys Val Ile Asn Asp Arg Glu Thr Gly Arg Ser
        35                  40                  45

Arg Gly Phe Gly Phe Val Thr Phe Ala Ser Glu Gln Ser Met Lys Asp
    50                  55                  60

Ala Ile Ala Gly Met Asn Gly Gln Asp Leu Asp Gly Arg Asn Ile Thr
 65                  70                  75                  80

Val Asn Glu Ala Gln Thr Arg Ala Ser Arg Gly Gly Gly Gly Gly
                 85                  90                  95

Gly Phe Gly Ser Gly Gly Gly Tyr Gly Gly Gly Arg Asp Arg Gly Tyr
                100                 105                 110

Gly Gly Asp Gly Gly Ser Arg Tyr Ser Arg Gly Gly Glu Gly Gly Gly
            115                 120                 125

Ser Asp Gly Asn Trp Arg Asn
    130                 135

<210> SEQ ID NO 39
<211> LENGTH: 836
<212> TYPE: DNA
<213> ORGANISM: Arabidopsis thaliana

<400> SEQUENCE: 39
cttcgtctac atcgttctac acatctcact gctcactact ctcactgtaa tcccttagat    60
cttcttttca aatttcaatg gcgtccggtg atgttgagta tcggtgcttc gttggaggtc   120
tagcatgggc cactgatgac agagctcttg agactgcctt cgctcaatac ggcgacgtta   180
ttgattccaa gatcattaac gatcgtgaga ctggaagatc aaggggattc ggattcgtca   240
ccttcaagga tgagaaagcc atgaaggatg cgattgaggg aatgaacgga caagatctcg   300
atggccgtag catcactgtt aacgaggctc agtcacgagg aagcggtggc ggcggaggcc   360
accgtggagg tggtggcggt ggataccgca gcggcggtgg tggaggttac tccggtggag   420
gtggtagcta cggaggtggc ggcggtagac gcagggtgag gaggatac agcggcggcg   480
gcggcggtta ctcctcaaga ggtggtggtg gcggaagcta cggtggtgga agacgtgagg   540
gaggaggagg atacggtggt ggtgaaggag gaggttacgg aggaagcggt ggtggtggag   600
gatggtaatt cctttaatta ggtttgggat taccaatgaa tgttctctct ctcgcttgtt   660
atgcttctac ttggttttgt gtgttctcta ttttgttctg gttctgcttt agatttgatg   720
taacagttcg tgattaggta ttttggtatc tggaaacgta atgttaagtc acttgtcatt   780
ctctaaataa caaatttctt cggagatatt atctctgttg attgattcta tcatct        836

<210> SEQ ID NO 40
<211> LENGTH: 176
<212> TYPE: PRT
<213> ORGANISM: Arabidopsis thaliana

<400> SEQUENCE: 40

Met Ala Ser Gly Asp Val Glu Tyr Arg Cys Phe Val Gly Gly Leu Ala
  1               5                  10                  15

Trp Ala Thr Asp Asp Arg Ala Leu Glu Thr Ala Phe Ala Gln Tyr Gly
                 20                  25                  30

Asp Val Ile Asp Ser Lys Ile Ile Asn Asp Arg Glu Thr Gly Arg Ser
             35                  40                  45

Arg Gly Phe Gly Phe Val Thr Phe Lys Asp Glu Lys Ala Met Lys Asp
     50                  55                  60

Ala Ile Glu Gly Met Asn Gly Gln Asp Leu Asp Gly Arg Ser Ile Thr
 65                  70                  75                  80

Val Asn Glu Ala Gln Ser Arg Gly Ser Gly Gly Gly Gly His Arg
                 85                  90                  95

Gly Gly Gly Gly Gly Gly Tyr Arg Ser Gly Gly Gly Gly Tyr Ser
                100                 105                 110

-continued

```
Gly Gly Gly Gly Ser Tyr Gly Gly Gly Gly Arg Arg Glu Gly Gly
            115             120             125

Gly Gly Tyr Ser Gly Gly Gly Gly Tyr Ser Ser Arg Gly Gly Gly
        130             135             140

Gly Gly Ser Tyr Gly Gly Arg Arg Glu Gly Gly Gly Gly Tyr Gly
145             150             155             160

Gly Gly Glu Gly Gly Gly Tyr Gly Gly Ser Gly Gly Gly Gly Trp
            165             170             175
```